United States Patent [19]
Sutcliffe

[11] Patent Number: 6,124,438
[45] Date of Patent: Sep. 26, 2000

[54] SYNTHETIC POLYPEPTIDES CORRESPONDING TO PORTIONS OF PROTEINOIDS TRANSLATED FROM BRAIN-SPECIFIC MRNAS, RECEPTORS, METHODS AND DIAGNOSTICS USING THE SAME

[75] Inventor: J. Gregor Sutcliffe, Cardiff, Calif.

[73] Assignee: The Scripps Research Institute, LaJolla, Calif.

[21] Appl. No.: 08/466,927

[22] Filed: Jun. 6, 1995

Related U.S. Application Data

[62] Division of application No. 08/116,873, Sep. 3, 1993, which is a division of application No. 07/476,961, Feb. 7, 1990, Pat. No. 5,242,798, which is a division of application No. 07/058,620, Jun. 3, 1987, Pat. No. 4,900,811, which is a continuation of application No. 06/516,136, Jul. 21, 1983, abandoned.

[51] Int. Cl.$^7$ .................................................. C07K 16/00
[52] U.S. Cl. ................................. 530/387.9; 530/388.1; 530/389.1
[58] Field of Search ................................. 530/300, 315, 530/316, 302, 324, 326, 387.1, 387.9, 388.1; 514/12, 13, 14, 15, 16, 17, 18, 19, 2; 435/7.1, 7.21, 7.9, 7.92, 7.94, 7.95, 40.5, 40.52

[56] References Cited

U.S. PATENT DOCUMENTS

| | | |
|---|---|---|
| 3,949,064 | 4/1976 | Bornstein et al. . |
| 4,205,057 | 5/1980 | Whitaker . |
| 4,237,224 | 12/1980 | Cohen et al. . |
| 4,312,857 | 1/1982 | Coy et al. . |
| 4,342,832 | 8/1982 | Goeddel et al. . |
| 4,350,627 | 9/1982 | de Castiglione et al. . |
| 4,350,764 | 9/1982 | Baxter et al. . |
| 4,388,236 | 6/1983 | Stein . |
| 4,389,342 | 6/1983 | Reinhard . |
| 4,401,759 | 8/1983 | Rubin et al. . |
| 4,415,558 | 11/1983 | Vale, Jr. et al. . |
| 4,416,988 | 11/1983 | Rubin . |
| 4,425,269 | 1/1984 | Christy et al. . |
| 4,430,428 | 2/1984 | Fraser et al. . |
| 4,457,917 | 7/1984 | Schaller . |
| 4,462,941 | 7/1984 | Lee et al. . |
| 4,469,631 | 9/1984 | Baxter et al. . |
| 4,481,191 | 11/1984 | Wei et al. . |
| 4,677,195 | 6/1987 | Hewick et al. . |
| 4,900,811 | 2/1990 | Sutcliffe . |
| 5,030,565 | 7/1991 | Niman et al. . |
| 5,242,798 | 9/1993 | Sutcliffe . |

FOREIGN PATENT DOCUMENTS 044 710 B2    6/1991    European Pat. Off. .

OTHER PUBLICATIONS

Dahl et al, Brain Research, 57:343–360, 1973.
Hycén, et al, Journal of Neurobiology, 9(6):489–492, 1978.
Lakin et al, Journal of Neurochemistry, 37(5):1170–1178, 1981.
Izant et al, Proc. Natl. Acad. Sci., 77(8):4741–4745, Aug. 1980.
Haan et al, Proc. Natl. Acad. Sci., 79:7585–7589, Dec. 1982.
Sutcliffe et al, Cell 33:671–682, July 1983.
Lai et al, Proc. Natl. Acad. Sci, 84:4337–4341, 1987.
Rueger et al, Analytical Biochemistry, 89:360–371, 1978.
Sato et al, Biochemical and Biophysical Research Communications, 163(3):1473–1481, Sep. 29, 1989.
Langley et al., Journal of Neurocytology, vol. 9, No. 6:783–798, 1980.
Poletaev et al, Bulletin of Experimental Biology and Medicine 83(2):152–154, 1977.
Ignator, S.A., ZH, Nervopat. Psikhiat, Korsakor 77(1):48–51, 1977.
Beck et al, Brain Research, 112:329–335, 1976.
Itoyama et al., Ann. Neurol, 7:167–177, 1980.
Sutcliffe et al, Cold Spring Harbor Symposium on Quantitative Biology. vol. 48. Molecular Neurobiology Conference Date Jun. 1, 1983, Pub date 1983, pp 477–484.
Hawkes et al Cell, 28:253–258, Feb. 1982.
Edelman, GM., Science, 219:450–457, Feb. 4, 1983.
Gheuens et al, Neuroscience Letters, Supplement 10 (1982):5205.
Östermann et al, Cell Tissue Res 228:459–473, Feb. 2, 1983.
Chem. Abstr., 81:625 (1974).
Chem. Abstr., 100:29938 (1984).
Chem. Abstr., 101:144699 (1984).
Chem. Abstr., 101:85984 (1984).
Chem. Abstr., 103:158508 (1985).
Chem. Abstr., 102:22043 (1985).
Ruggiero et al. *Submicrosc. Cytol,* 16(1):131–134 (1984).
Valdivia et al., *Biochem. biophys. Res. Commun.,* 105(4):1241–1249 (Apr. 29, 1982).
Lakin et al., *J. Neurochem.,* 41:385–394 (1983).
Flanagan et al., *J. Neurochem,* 46(2):542–544 (1986).
Ripellino et al., *J. Neurochem.,* 53:1103–1108 (1989).
Green et al., *Cell,* 28:477–478 (Mar. 1982).
Sutcliffe et al., *Science,* 219:660–666 (1983).
Sutcliffe et al., *Cell,* 33:671–682 (1983).
Milner et al., *Nucleic Acids Res.,* 11(6):5497–5520 (1983).
Guillemin, *Science,* 202:390–402 (1978).
Bantle et al., *Cell,* 8:139–150 (1976).
Hastie et al., *Cell,* 9:761–774 (1976).
Sutcliffe et al., *Proc. Nat'l. Acad Sci. U.S.A.,* 79:4942–4946 (1982).

(List continued on next page.)

*Primary Examiner*—Patricia A. Duffy
*Attorney, Agent, or Firm*—Welsh & Katz, Ltd.

[57] ABSTRACT

Antibodies or epitope-binding portions thereof raised to a synthetic polypeptide having an amino acid sequence that corresponds substantially to an amino acid residue sequence of at least a portion of a naturally occurring proteinoid and having a molecular weight equal to less than that of the proteinoid are diclosed. That proteinoid contains an amino acid residue sequence translated from a messenger RNA present substantially only in brain cells. Those antibodies or epitope-containing portions bind specifically when admixed with brain cell tissue that includes the naturally occurring proteinoid.

10 Claims, 21 Drawing Sheets

OTHER PUBLICATIONS

Southern, *J. Mol. Biol.,* 98:503–517 (1975).
Gros et al., *Molecular Genetic Neuroscience,* Schmidt, Bird and Bloom, eds., Raven Press, New York 335–347 (1982).
Cleveland et al., *Cell,* 20:95–105 (1980).
Green et al., *Cell,* 28:477–487 (1979).
Naranishi et al., *Nature,* 278:423–427 (1979).
Amara et al., *Nature,* 298:240–244 (1982).
Land et al., *Nature,* 295:299–303 (1982).
Kakidani et al., *Nature,* 298:245–249 (1982).
Towbin et al., *PRoc. Natl. Acad. Sci. USA,* 76:4350–4354 (1979).
Elder et al., *Proc. Natl. Acad. Sci. USA,* 79:4540–4544 (1982).
French et al., *Regulatory Peptides,* 1:127–146 (1980).
Koob et al., *Regulatory Peptides,* 2:153–163 (1981).
Barnstable, *Nature:* 286:231–235 (1982).
Thomas, *Proc. Natl. Acad. Sci. USA,* 77:5201–5205 (1980).
Rigby et al. *J. Mol. Biol.,* 113:237–251 (1977).
Laemmli, *Nature,* 227:680–682 (1971).
Tanaka et al., *J. Bacteriol.,* 121:354–362 (1975).
Sutcliffe, *Nucleic Acid Res.,* 5:2721–2728 (1978).
Maxam et al., *Proc. Natl. Acad. Sci. USA,* 74:560–564 (1977).
Bittle et al., *Nature,* 298:30–33 (1982).
Bloom et al., *Proc. Natl. Acad. Sci. USA,* 75:1591–1595 (1978).
Schibler et al., *J. Mol. Biol.,* 142:93–116 (1980).
Aviv et al., *Proc. Natl. Acad. Sci. USA,* 69:1408–1412 (1972).
Wickens et al., *J. Biol. Chem.,* 253:2483–2495 (1978).
Gough et al., *Biochemistry,* 19:2702–2710 (1980).
Jacobsen et al., *Eur. J. Biochem.,* 45:623–627 (1974).
Roychoudary et al., *Nucleic Acids Res.,* 3:865–877 (1976).
Birnboim et al., *Nucleic Acids Res.,* 7:1513 (1979).
Rave et al., *Nucleic Acid Res.,* 6:3559–3567 (1979).
Denhardt, *Bichem. Biophys. Res. Comm.*m 23:641–646 (1966).
Melli et al., *J. Mol. Biol.,* 93:23–38 (1975).
Dermen et al., *Cell,* 23:731–739 (1981).
Rivier, *J. Chromatogr.,* 202:211–222 (1980).
Arnheiter et al., *Nature,* 294:278–280 (1981.
Bodor, *Science,* 214:1380–1372 (1981).
Tachibana et al., *Nature,* 295:339–340 (1982).
Goedert et al., *Develop. Brain Res.,* 200:127–131 (1985).
Rivier et al., *Fed. Proc.,* 44:189–195 (1985).
Herbert, *Trends in Biochemical Science,* 6:184–188 (1981).
O'Sullivan, *C & EN,* pp. 26–27 (Nov. 15, 1976).
Numa et al., *Trends in Biochemical Science,* 6:274–277, (1981).
Noda et al., *Nature,* 297:431–434 (1982).
Comb et al., *Nature,* 295:663–666 (1982).
Gubler et al., *Nature,* 295:206–208 (1982).
Rossler et al., *Nature,* 298: 221–222 (1982).
Marx, *Science,* 220:395–397 (1983).
Meisenberg et al., *Life Sciences,* 32:2611–2623 (1983).
Goldstein, *Science,* 193:1081–1086 (1976).
Brilliant et al., *Mol. Cell Biol.,* 4:2187 (1984).
Kreiner et al., *J. Neurosci.,* 4:2581 (1981).
Schmidt, *Neuroscience,* 13:991 (1984).
Petrusz et al., *Fed. Proc.,* 44:299 (1985).
W. Broad and N. Wade, *Betrayers of the Truth,* Simon and Schuster, New York (1982) p. 54.
Cole et al., *Science,* 178:368–375 (1972).
Hidaka et al., *J. Biol. Chem.,* 258:2705–2709 (1983).

FIG.1C-1

```
            orf 1
            TyrLysValTyrLysTyrAspArgAlaCysProAspGlyPheValLeuLysAsnThrGlnCysIleProGlyGlyLeuGluSerTyrTyrThrGluGlnAspSerSerA
CTGCA(G)12 TACAAAGTGTACAAGTATGACCGTGCGTGCCCTGATGGGTTTGTCTTGAAGAATACCCAGTGCATCCCAGGAGGCTTGGAGAGCTACTACACGGAGCAAGACTCCAGTG
                                                                         P1
laArgGluLeuLysPheTyrThrValIleAsnHisTyrAsnLeuAlaLysGlnSerIleThrArgSerValSerProMetSerValLeuSerGluGluLysLeuSerGluGlnGluThrG
CCCGGGAGAAATTTACACTGTCATAAATCACTACAACCTGGCCAAGCAGAGCATCACGCGCTCAGTGTCACCGTGGATGTCAGTTCTGTCAGAGAGAAGAGCTGTCGGAACAGGAGACCG
                                P2
luAlaAlaGluLysSerAla***
AAGCTGCAGAGAAGTCAGCTTAGCAAGCGGGGGCAGGTTCCTTACAATGTGTCACTTGAAGGCAACAAGGGACTTTGAGGGACATTTCATTAAATATAATTACCGATAATTAGAGATTA CTCATTTACGGTGCAATTGCTTCTGTTGCTAATGCTGCTTGCAAATAAAACTTGCTGCGGACCACCCACAGGCATAAGAAAAGTGCATCTCAGCACTGCTTAGAGAGCTTGATGCCAC
```

FIG. 1C-2 orf 2

MetProGlyLeuArgProSerGluGlnCysIleTrpTrpPhe
TGTCCATGCCGAGGAGTCGCCATTAGCTCCTTCACTGGGACGCACTGGATACTGTCAAGAGGTAATTCGCCCTGGCTATGCCAGGGCTCCGGCCATCAGAACAGTGCATTTGGTGGTTT

P3
ArgSerLeuLeuCysProPheAlaIleCysArgProTyrProIleHisArgValThrProArgSerAlaAspCysSerValAspAlaLeuLeuSerGlyAlaLaGluGlyArgCysAla
CGTTCTCTTTTATGCCCCCTTTGCTATTTGCAGACCTTACCCATACATAGAGTGACCCCACGCTCTGCTGACTGCAGTGTGCAGTGCACTGCTAAGCGGGCAGAGGAAGGAAGGTGTGCA

ProArgHisThrGlnProCysGlnGlySerSerGlyArgPheSerLeuLeuCysProLeuArgArgThrArgArgGlyTrpGlyGlyGluLeuAlaLeuLeuGlyGlnGlyValAlaGluPro
CCACGACACGCAGCCCTGCCAGGGCAGTTCTGGGAGGTTCTCTCTTTGTCCCTGCCAGAACACGGAGGAGCTGGCTCTGGGCCAGGGGTTGCCGAGCCT

ValLeuLeuTrpValValSerAlaGlyAspValLeuAspArgLysLysAlaHisTrpLeuValProPheLeuLeu***
GTGCTCTGTGGGTGGTGTCTGCTGGTGATGTGCTAGATAGGAAGAAGGCCCACTGGCTCGTTCCTTCCTTGTTATGATACATTTGCACGTACAGCCCTGAATGCAGGTGCAGTTTTGGT

TTTTGTTTTCTTAGCCAGTGGGCAAAGTGAAATGTAATTTTGGGTAAGCCAGGGCTTCTTAGCTTTTATTCTGTGAACAGATGTGACTCCTGTGCTGTGGGAAGGGGGCAGGACGGCT

GGTGGGGGCTGATGTGGCACCCTTGAAAATAGAATAAGTCCACAATCTTTGTAAGAAAAGAACCCCG(C)$_{15}$TGCAG

```
                      ThrGluSerProSerPheSerAlaGluAspAsnProHisValLeuTyrSerProGluPheArgIleSerGluAlaAlaProAspLysTyrGluSerProAspLysTyrGluLysArgLeuGlySerGluArgAr
                      ACAGAGAGCCCCAGCTTCTCAGCGGGAGACAACCCTCATGTCCTGTACAGCCCTGAATTCCGAATCTCTGGAGGCTGCTCCTGATAAGTATGAGAGTCCTGATAAGTAGAAGCGCCTGGGGTCCGAGAGGAG
                      P5                                                                                                    P7
                      gLeuLeuGluArgGlyGluGlyProProGluLeuAspLeuSerTyrSerHisSerAspLeuLysLysArgProThrLysAspSerTyrThrLeuThrGluGluLeuAlaGluTyrAlaG
                      GCTGCTGGGCTTAGGGGAGAACCCCCAGAACTGGACCTCAGTTATTCCCACTCAGACCTGGGGAAACGACCCCACCAAGGACAGCTACACCCTGACAGAGGAGCTGGCTGAGTACGCAG
                      LuIleArgValLys***
                      AAATCCGAGTCAAGTGAGGAAGCTGGGGGCTGGCCCGTGGCTCACCCCCCATCAGGACCCTCGCTTGGCCCTGGCCGTGGGCTCCCTTTCTCTTGAGAGTGGTAGGGTGGGGG

CGGGAAGGGGCAGGAAACAGTGAGGTCTTAGGGCCCCTCCCCTTCCCGGTGCTCCTCCTCTGCCAACATCCTGCACCTATGTTACAGCTCCTCCCCTCCTTTA

ACCTCAGCTGTTGAGAGGGGTGCTCTGTCTCTGTCCATGTTATTATTGTTATCCTGGTCTCCCCTTACCCGGCCCCAGGACCTGTACAAAGGGACATGAAATAAATGTCCTAAT

GACAAGTGCCAGTCTAGACCCATCCTTTGGGAGGAAAGGGGCATATTAGTAATACTTTTCTGTTGCTGTAACAAAATACTGGACAAAAAACAC(A)-100(C)n
```

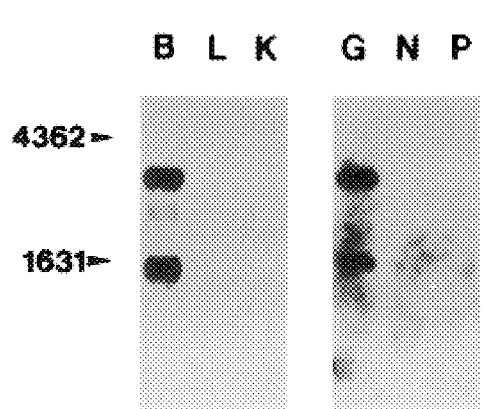
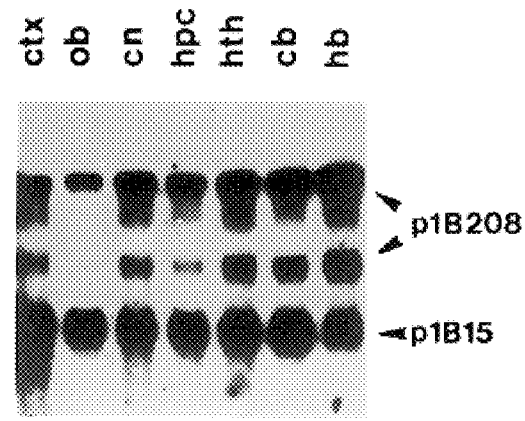
FIG.7A     FIG.7B
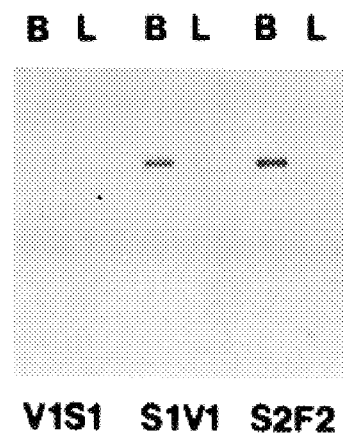
FIG.7E

TCTTCTTACTTGATGAGTATAACAGAAGGAGAGTATTGCAGTGATTAATCTCTCTGTGGACTCTCCCTCTTATGTACCTCTTTCAGTCATTTTGCTCCACAGTGGGCTCCTGCTA

GAAATGGGAATACCTGAGAAGGTGATTCCCCGCTGCAAGTCGCAGAGGAATGAAAGCTCTAATTGAGTTTGCAAGCATCCTGAAGGCCAGGATGTGCTTCCTTCTCAAAGGGCAC

TTCCATTGAGGAAACAAAGTGGAAAGAAAGATTCTCAGGTAGAAAGCAGGAATGTCCTTGGTCTCCTTGCCATCAGTAGGAGTCAAATATATTCTCTTTGATGCACAAAACCAAGAAC

TCACTCTTTCTTCCTAGTTCCACTGAAGACAGAAGGAAATAAGCCAATAGCATTTGCCCAAATCTGCCTCCTGCAGCTAGGAGAAGGGGTCAAAGCAAGGATCTTTCACCCTTAGAAA

GAGAGCTCTGACGCCAGTGGCAATGGACTATTTAC$_{13}$TGCAG

FIG.8B-1

CTGCAG,₅CCGGCAGCCCTGCCTCTTCCTTTTAATTTCTCCTTCCCGAGGCAGCTTCACAGACCCATCCCCAGACTGTTCACAGACCAGTGCGGAGAGGGTCCTCTGTCCCTGTGAC

CCTGTGATCCGGGCAGCTCAGTGTCCCTGCCCCACCTCCCCAGGTGGCATTAATCAGCAAACAGCCTATCCAGAAGAGCTCTGTGTGCTGAGGAGAAAAGAAAGCCACAAGCACAA

TTGCCTTTTCTGGTCACCAACCCAGGACTTTCCCCGAGTGGGAGCTGTAGTCCCTCTGAGCTGCCCAGTTAACACAAACAATGGCCAAGGAAATCAAGGTGAAGGTTCTAAGTCAGGA

CCAATCCAGCCACCCTGGTTCCCTCTTAGACTGTCACTGCCACTCTGTTCTGCTCCTTACCTTTCTGAAAACTTTCAGATGTACACCCCACTAACGGAGGAG

GGTTACTTCAGAGGTTCCCTCCATCCTACCCTGAGCTTCCCCTGCTCCAGTGGGAGCATCGTATGTCCCTTCTGGCCTTGGATTCTGTGTTGGTGAAGCCAGTGGAGACAGT

TTCTGGAAAGTTCCAGCAGCTCCGTCTTTCTCCTCTGCCGAGAGGATGGACTCCCATGTAGCAAAGCGTATATGTCTTGTCCCGTAGCTGGAAGCTCACAAACTGTGTTTATG

FIG.8B-2

ACTAATCCTTAATAACTATGGTGAATAACTGTGACCGTGGGTTTCTTGAATCTCTTGTCATTCTCATCCAAAAGTGACCAGCACACCAGTTCTTGCAATAAGCTATCTCCCTCCCTCAG

AGCATCAAGCACACTGTAGAGAATGCAAACACGTACGCACATAGAAATGCACACACATGCATACCCATCCTCACATGTGGCAGTTAGCGTCCCGTGTGATATTGTGTAGGCAATCTACC

AGCTCTTCCCGAGGCCACTTGTAGCAGGGTCGTGTGGCTGAGGCATCTGCCTGCTCAGTGGAGACTCTGCGACCAGCTTGCACAGGTGCCTGTCGCCAGAGTCCCAGGTGTGGAATGCA

AGGACCCCTCCACTGTCTCGTGGCCCCGTCCCTCCCCTACCTGTCTATGAAGCCCTTTAGGATGAAGGCAGGAGGTTCCTTCTTCTTGCTCGTCGATGTTCTTTGATGGAAAACTGAGAA

CAAGTCTTTTTGAGATAAATGCAGTC$_{13}$TGCAG

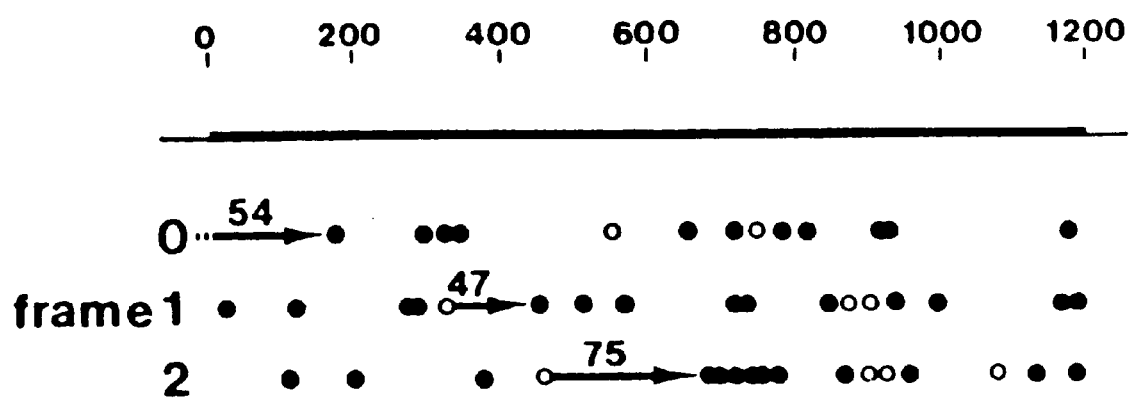

SYNTHETIC POLYPEPTIDES CORRESPONDING TO PORTIONS OF PROTEINOIDS TRANSLATED FROM BRAIN-SPECIFIC MRNAS, RECEPTORS, METHODS AND DIAGNOSTICS USING THE SAME

CROSS-REFERENCE TO RELATED APPLICATIONS

This is a division of application Ser. No. 08/116,873, filed Sep. 3, 1993, which is a division of application Ser. No. 07/476,961, filed Feb. 7, 1990, now U.S. Pat. No. 5,242,798, that was a division of application Ser. No. 07/058,620, filed Jun. 3, 1987, now U.S. Pat. No. 4,900,811, that was a continuation of Ser. No. 06/516,136, filed Jul. 21, 1983, now abandoned.

DESCRIPTION

1. Technical Field

The present invention relates to synthetically prepared polypeptides, and more specifically to synthetic polypeptides whose amino acid residue sequences correspond to the sequences of materials that are translated from messenger RNA molecules located substantially only in the brain.

2. Background Art

A key to understanding the function of any tissue is the biochemical characterization of the proteins that are specific to that tissue. The mammalian brain is composed of two predominat cell types, neurons and glia, which are organized into a great variety of structures. Whether the brain is viewed as one or several tissues, its organization involves many cells that are believed generally to perform the same physiological actions but at different places and in response to different signals. Accordingly, one can expect to find a large number of brain-specific proteins in a mature brain, including those involved in both specialized and general brain processes.

Exemplary of specifiable brain-specific proteins are: neuropeptide precursors, enzymes responsible for neurotransmitter synthesis and/or processing, proteins that participate in the release, degradation or reuptake of neurotransmitters, signal receptor systems and ion channels. Proteins included in the basic cellular structures include those peculiar to neurons (axons, dendrites and synapses) and those involved in establishing specific cell-cell interactions. Also, there will be proteins involved in mental processes such as memory which are not at all yet understood at the cellular, let alone molecular level. Clearly, the brain is a difficult tissue to study at the molecular level due to its great complexity.

Conventional protein chemistry is unsuitable for defining rare, unique proteins or structures present in very small regions of the brains. Furthermore, approaches at the protein chemical level are dependent on having a suitable assay for each protein, which is usally not generalizable to other molecules, and which approach will clearly only be applicable to molecules that fit an existing conceptual framework, such as the hypophysiotrophic factors. Guillemin, Science, 202, 390–402 (1978).

It is presumed, however, that all of the proteins of the brain are synthesized by translation from specific messenger RNA (mRNA) molecules, and thus each brain-specific protein must have a corresponding mRNA. Thus, one approach to the study of the brain is through the transcription pattern of messenger RNA (mRNA) molecules, or by asking the question of what messenger RNA species the brain produces relative to its complete genomic potential. Estimates for the complexity of mammalian brain-specific mRNAs are very high; tens to hundreds of thousands of discrete mRNA molecules are implicated in brain function [Bantle et al., Cell, 8, 139–150 (1976) and Hastie et al., Cell, 9, 761–774 (1976).], consistent with the variety of brain-specific proteins listed above.

BRIEF SUMMARY OF THE INVENTION

In accordance with the present invention, a synthetic polypeptide is prepared substantially corresponding in amino acid residue sequence to at least a portion of the sequence of a naturally occurring proteinoid, and having a molecular weight equal to less than that of the proteinoid. The proteinoid itself contains an amino acid residue sequence that is translated from a messenger RNA present substantially only in brain cells. The messenger RNA is typically polyadenylated and is present in the cytoplasm of the brain cell tissues. The synthetic polypeptide of this invention linked to a carrier as a conjugate and introduced as that conjugate into an animal induces. the production of antibodies that bind to the naturally occurring proteinoid or a derivative of that proteinoid as well as binding to the synthetic polypeptide to which those antibodies were induced.

In another embodiment of this invention, the synthetic polypeptide is introduced into an animal alone or as a conjugate bound to a carrier to induce in that animal the production of antibodies to the synthetic polypeptide. After harvesting the antibodies so induced, the harvested antibodies or idiotype-containing polyamide portions of those antibodies, collectively referred to herein as receptors, are admixed with brain cell tissue and an indicating group to assay for the presence of an amino acid residue sequence of a naturally occurring proteinoid present in said brain tissue; the indicating group indicating the formation of an immune reaction between a proteinoid or its derivative containing the amino acid residue sequence assayed for and the receptor.

A further embodiment of the present invention is a diagnostic system for assaying for the presence of a naturally occurring amino acid residue sequence of a proteinoid present in brain cells by the formation of an immune reaction. This system includes at least one package containing a biologically active receptor that includes an antibody or idiotype-containing polyamide portion of an antibody raised to the synthetic polypeptide of this invention or to a conjugate of that polypeptide bound to a. carrier. An indicating group or label is utilized to indicate the formation of an immune reaction between the receptor and the proteinoid or derivative thereof containing the amino acid sequence assayed for when the receptor is admixed with brain tissue.

A still further embodiment of the present invention contemplates a pharmaceutical composition that contains as an active ingredient an effective amount of a synthetic polypeptide of this invention or a lipophilic derivative of such synthetic polypeptide. The lypophilic synethetic polypeptide derivative is capable of passage from the blood stream through the blood-brain barrier and into brain cell tissues. The pharmaceutical composition also contains a pharmaceutically acceptable diluent.

Yet another embodiment of the invention is a method for determining whether an injury has occured to an animal's brain tissue by the formation of an immune reaction. Here, cerebrospinal fluid from an injured animal suspected of having injured brain tissue and containing a proteinoid or a proteinoid derivative released from the injured brain tissue is provided. An aliquot of that cerebrospinal fluid is admixed with effective amounts of (i) a biologically active receptor and (ii) an indicating group. The receptor is an antibody or idiotype-containing polyamide portion of an antibody raised to a synthetic polypeptide of this invention. The admixture is then assayed for the presence of an immune reaction between a proteinoid or its derivative in the cerebrospinal fluid and the receptor. The presence of an immune reaction is indicated by the indicating group, with that immune reaction being indicative of an injury to the brain tissue containing the proteinoid or its derivative.

A diagnostic reagent that binds to specific brain tissue comprises yet another embodiment of the present invention. This reagent is a biologically active receptor that can be linked to an indicating group. The receptor is an antibody or idiotype-containing portion of an antibody raised to a synthetic polypeptide or conjugate of that synthetic polypeptide bound to a carrier. An immune reaction is formed when the receptor is admixed with brain cell tissue that includes a naturally occurring proteinoid or a derivative thereof. The indicating group bound to the receptor or as an exogenously supplied reagent indicates the formation of an immune reaction between the receptor and brain tissue containing the proteinoid or its derivative. In preferred practice, the proteinoid is translated from an mRNA that is present substantially only in brain cell tissue from a known type of brain cell tissue.

The present invention provides several benefits and advantages. More particularly, the invention provides useful probes through a synthetic polypeptide and the receptor molecules made therewith into the structure and function of brain cells. Thus, as one of its benefits, it is now possible to determine the presence of particular amino acid residue sequences in brain cell tissues.

Another of the benefits of the invention is the provision of a diagnostic system for assaying the presence of a naturally occurring amino acid residue sequence of a proteinoid present in brain cells.

Yet another benefit of the present invention is the provision of a biologically active receptor that immunologically reacts with brain cell tissues that include particular amino acid residue sequences.

A still further benefit of the invention is a method by which the presence of an injury to brain cell tissue may be determined.

One of the several advantages of the present invention lies in the provision of a pharmaceutical composition that contains a synthetic polypeptide of this invention present in its free form, or as a lipophilic derivative that is capable of passage from the blood stream through the blood-brain barrier and into the brain cell tissues.

Still further benefits and advantages of the present invention will be apparent to those skilled in the art from the detailed description and claims that follow.

BRIEF DESCRIPTION OF DRAWINGS

FIG. 1 illustrates the characterization of the plA75 complementary deoxyribonucleic acid (cDNA) of clone plA75.

FIG. 1C illustrates the nucleotide sequence of the sense strand of clone plA75. The sense strand of the clone is shown having the 5' terminus proximal to the Eco RI cleavage site of plasmid pBR322. Also illustrated above the nucleotide sequence are the two putative open reading frames (orf 1 and orf 2) shown as the translated amino acid residue sequences. Three polypeptides (P1, P2, P3) selected for use in raising antibodies are underlined in the amino acid residue sequences.

FIG. 2 illustrates the characterization of the protein corresponding to the translation product of clone plA75.

FIG. 3 illustrates the immunocytochemical detection of rat brain antigen with pIA75 antipeptide antisera. Staining was done as described in the Materials and Methods section, hereinafter. All primary antibodies were used at a final dilution of 1:500. The same anti-P1 pattern was observed at dilutions up to 1:20,000.

FIG. 4 illustrates the characterization of clone P1B236.

FIG. 4C illustrates the nucleotide sequence of the pIB236 cDNA insert showing the long open reading frame and the positions of synthesized polypeptides P4, P5, P6 and P7. The 5' terminus is proximal to the Eco RI cleavage site of plasmid pBR322. Details are as described in FIG. 1C.

FIG. 6 illustrates the immunocytochemical detection of rat brain antigen with pIB236 antipeptide antibodies.

FIG. 6A is a photomicrograph illustrating a low power view of cerebellum cells stained with anti-P5 antiserum showing fiber tracts: molecular (M), Purkinje cell layer (P), granule cell layer (G) and white matter (WM). The bar equals 500 microns.

FIG. 6B is a photomicrograph illustrating an enlarged view of cerebellum cells showing the region boxed in FIG. 6A. Radial and tangential fibers in the molecular layer are indicated by arrows. Other details are as in FIG. 6A. The bar equals 25 microns.

FIG. 6C is a photomicrograph illustrating fibers in the $CA_3$ region of the hippocampus stained using anti-P5 antiserum. Abbreviations: molecular layer (M) and pyramidal cell layer (P). The bar equals 50 microns.

FIG. 6E is a photomicrograph illustrating fibers in the cingulate cortex stained using anti-P5. Tangential fibers in layer 1 (indicated by a vertical bar) and radial fibers in deeper layers are shown. The horizontal bar in the lower left corner equals 50 microns.

FIG. 6F is a photomicrograph illustrating fibers in cingulate cortex stained using anti-P6 antibodies. The region of cortex shown is deeper than the view in FIG. 6E. The bar equals 50 microns.

FIG. 6G is a photomicrograph illustrating staining in deep cerebellar nuclei using anti-P5 antibodies and showing intense peripheral staining of large cell bodies. The bar equals 50 microns.

FIG. 6H is a photomicrograph illustrating a low power view of cell bodies stained using anti-P5 antibodies from the brain stem of a colchicine-treated rat. The bar equals 100 microns. Insert FIG. 6Ha is a photomicrograph illustrating an enlarged view of the cell bodies in FIG. 6H. The bar equals 25 microns.

FIG. 7 illustrates the characterization of clone 1B208.

FIG. 7A is a photograph of the autoradiogram illustrating Northern blot analysis of the tissue distribution of pIB208 mRNAs. Details are as described in FIG. 1A.

FIG. 7B is a photograph of an autoradiogram illustrating Northern blot analysis of the regional distribution of pIB208 mRNAs and pIB15 mRNA in rat brain. Details are as described in FIG. 1B.

FIG. 7C illustrates the nucleotide sequence of the sense strand of the pIB208 cDNA insert showing the translated open reading frame. The 3' terminal end of the insert sequence is proximal to ECO RI cleavage site of plasmid pBR322. Details are as described in FIG. 1C.

FIG. 7E is a photograph of an autoradiogram illustrating detection of pIB208 mRNAs by single end-labeled restriction fragments prepared as indicated in FIG. 7D. Fragment VIS1 was slightly contaminated with fragment VIS2 producing some detection of the larger pIB208 mRNA. Details are as described in FIG. 1E.

FIG. 8 illustrates the characterization of clone p0-40.

FIG. 8B illustrates the nucleotide sequence of the sense strand of the p0-40 cDNA clone insert. The 5' terminus is proximal to the Eco RI cleavage site of plasmid pBR322. Details are as described in FIG. 1B.

FIG. 8C illustrates the possible open reading frames of p0-40. The sense strand of the cDNA insert (thick line) is represented, at the top of the Figure. Below, in the three possible reading frames of the sense strand, the positions of initiation codons are indicated by open dots (o) and termination codons are indicated by darkened dots (●). Also illustrated are the positions and lengths (in triplets) of the largest orf in each frame.

DETAILED DESCRIPTION OF THE INVENTION

Figures 1A, 1B:
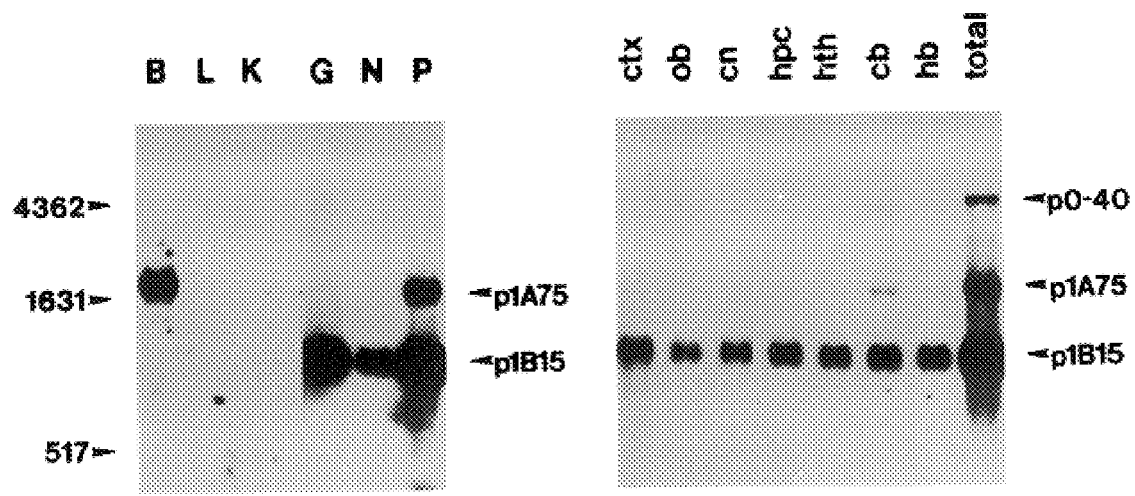
FIG. 1A is a photograph of an autoradiogram illustrating Northern blot analysis of the cDNA clone plA75 messenger ribonucleic acid (mRNA). Two micrograms each of polyadenylated messenger RNA [poly (A)$^+$ mRNA] from rat brain (B), rat liver (L), rat kidney (K), rat glioma (G), mouse neuroblastoma (N) and rat pheochromocytoma PC12 (P) were separated by electrophoresis on 1.5 percent agarose gels, blotted to nitrocellulose and hybridized with $^{32}$P-labeled plA75, or hybridized with a mixture of $^{32}$P-labeled plA75 and plB15. The positions and lengths of DNA size markers are shown at the left.
FIG. 1B is a photograph of an autoradiogram illustrating Northern blot analysis of the regional distribution of plA75, pO-40, and plB15 mRNAs. 20 Micrograms each of cytoplasmic mRNA from cortex (ctx), olfactory bulb (ob), caudate nucleus (cn), hippocampus (hpc), hypothalamus (hth), cerebellum (cb) and pons/hindbrain (hb) and 2 micrograms of brain (total) poly (A)$^+$ mRNA were separated on a 1.5 percent agarose gel and the mRNAs specific for each clone (indicated at the right) were detected as in FIG. 1A.
Figure 1E:
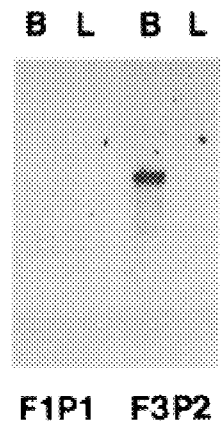
FIG. 1E is a photograph of the autoradiogram illustrating detection of plA75 mRNA by single end-labeled restriction fragments of the plA75 cDNA insert. Two micrograms each of poly (A)$^+$ mRNA of rat brain (B) and rat liver (L) were analyzed by Northern blotting using single end-labeled restriction fragments F1P1 and F3P2 prepared as shown in FIG. 1D.

The present invention contemplates synthetic polypeptides, as well as products and methods obtained from their use. The synthetic polypeptides of this invention have amino acid residue sequences that correspond to at least a portion of the sequence of a naturally occurring proteinoid and have a molecular weight equal to less than that of the proteinoid.

The proteinoid amino acid residue sequence to which the sequence of the synthetic polypeptide corresponds is translated from a messenger RNA that is present substantially only in brain and/or spinal cord cells. Since the brain and spinal cord are so intimately related, these mRNA molecules are referred to herein as being brain-specific or as being present substantially only in the brain with the understanding that they may also be present in the spinal cord. Thus, the naturally occurring proteinoids, proteins and polypeptides having amino acid residue sequences corresponding to those of the synthetic polypeptides of this invention are themselves manufactured substantially only in brain cell tissues. This is in contradistinction to materials such as somatostatin, thyrotropin-releasing factor (TRF), luteinizing hormone-releasing factor (LRF), the endorphins and enkephalins, or the several other small polypeptides such as bombestin, caerulein or physalamine that have been found to occur in the brain as well as in other tissues of the animal body. [Guillemin, Science 202, 390–402 (1978).]

Definitions for several words and phrases used herein are given immediately below followed by a general discussion of the methods useful in this invention which itself is followed by a discussion of specific embodiments.

Proteinoid—The term "proteinoid" is used herein to mean the direct polypetide translation product of a messenger RNA, and may have a molecular weight of from about 600 through about 1,000,000, and possibly larger. The proteinoid may be a single protein or a fusion product of (a) a plurality of proteins that is subsequently processed by the brain cell into a plurality of cellularly useful proteins, (b) a fusion product of a plurality of polypeptides that is subsequently processed by the brain into a plurality of cellularly useful polypeptides, or (c) a fusion product of one or more proteins with one or more polypeptides that is subsequently processed into cellularly useful materials.

Proteinoid derivative—The phrase "proteinoid derivative" is used herein to mean the polypeptide-containing material that results from cellular processing of a proteinoid. A proteinoid derivative may therefore be a protein cleaved by cellular action from a fusion product containing a plurality of proteins, a polypeptide containing about six to about eighty amino acid residues that has neuroactivity, or the like. In addition, a proteinoid derivative may be a glycosylation product of the whole or a smaller proteinoid, or the product of a transamidification-deletion reaction or the like.

Immune reaction—The phrase "immune reaction" is used herein to mean the binding of a ligand with its receptor and includes the binding between an antigen (ligand) with an antibody (receptor) as well as between an antigen and an idiotype-containing polyamide portion of an antibody (receptor).

Corresponds substantially—The phrase "corresponds substantially" as used herein in conjunction with amino acid residue sequences means that the amino acid residue sequence of a first polypeptide is sufficiently similar to the amino acid residue sequence contained in a second polypeptide so that antibodies to the first polypeptide (e.g. synthetic polypeptide) form an immune reaction with the second polypeptide (e.g. proteinoid or derivative) when admixed in an aqueous medium. The preparation of such polypeptides and antibodies are discussed hereinafter in the Materials and Methods Section.

The epitope-containing amino acid residue sequence portions of the above two polypeptides, e.g. synthetic polypeptide and proteinoid, are most preferably identical, but conservative changes in amino acid residues and deletions or additions of amino acid residues within the epitope may be made and still permit the cross-reaction of an antibody to the first polypeptide with the second polypeptide, as is known. Conservative amino acid residue changes are well known, and include exchanges of residues such as between lysine and arginine, between aspartic acid and glutamic acid, between leucine and isoleucine, and the like.

The full names for individual amino acid residues are used herein as are the well-known three-letter abbreviations and one-letter symbols. The Table of Correspondence, below, provides the full name as well as the abbreviation and symbols for each amino acid residue named herein.

Table of Correspondence

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The following discussion outlines procedures that are useful in identifying proteinoids that are translated from brain-specific messenger RNA (mRNA), and for preparing synthetic polypeptides whose amino acid residue sequences correspond substantially to the amino acid residue sequences of at least a portion of those proteinoids, as well as the manufacture of receptor molecules from those synthetic polypeptides.

I. GENERAL APPROACH

The complexity of messenger RNAs expressed in the brain is higher than in other tissues, consequently a large number of tissue specific mRNA molecules may be easily identified. In addition, because the proteins of eukaryotes are colinear with their mRNA, but not necessarily colinear with their genes, brain mRNA, rather than genomic DNA is an appropriate starting point for study.

The adult male rat was chosen herein as a model since it is extensively used for behaviorial, neurophysiological, biochemical and neuranatomical studies. In addition, the similarity of brain tissue structure and function among the mammals permits extrapolation of useful results from the rat to humans and other mammals, as is known.

The cytoplasmic poly(A)+ mRNA from the brains of adult male Sprague-Dawley rats was purified and then converted into complimentary DNA (cDNA). The cDNA, after size enrichment and anealing to the Pst I site of plasmid pBR322, was then used to transform *Eschericia coli*. Recombinant plasmid DNA was isolated from small overnight cultures of individual cDNA clones, radioactively labeled by nick translation, and was used to probe for complimentary mRNA sequences on Northern blots with samples of brain, liver and kidney poly(A)+ mRNA.

The hybridization patterns of the cDNA clones fell into four classes: those hybridizing equally to all three tissues (Class I; 18%); those hybridizing differently to the three tissues (Class II; 26%); those hybridizing only to brain mRNA (Class III; 30%); and those showing no detectable hybridization (Class IV; 26%).

Tables 1–4 (below) list the clones prepared as classified by the tissue distribution patterns of the mRNAs they detected. These data are summarized in Table 5 (below).

The abundance of the mRNA molecules corresponding to several of the clones was independently assessed by hybridizing alkali-broken $^{32}$P-end-labeled poly(A)+ brain mRNA to excess purified plasmid DNA. Those results are also shown in Tables 1–4 hereinbelow.

TABLE 1

Characterization of Class I Clones

| Clone | Relative Abundance[1] | mRNA Size[2] |
|---|---|---|
| 1B211 | 3.0 | 600 |
| 1B447 | 2.0 | 1300 |
| 1B364 | 1.0 | 800 |
| 1B15 | 1.0 | 1000 |
| 1B258 | 1.0 | 1300 |
| 1A559 | 0.5 | 600 |
| 1B359 | 0.5 | 1500 |
| 1B372 | 0.5 | 2400 |
| 1B203 | 0.2 | 400 |
| 2A154 | 0.2 | 700 |
| 2A111 | 0.1 | 1200 |
| 1B268 | 0.1 | 1400 |
| 1B334 | 0.1 | 1400 |
| 1B374 | 0.1 | 1500 |
| 1A124 | 0.1 | 2000 |
| 1A71 | 0.1 | 3200 |
| 1B365 | 0.05 | 650 |
| 1B368 | 0.05 | 1000 |
| 1B435 | 0.05 | 1200 |
| 2A361 | 0.05 | 1500 |
| 1B446 | 0.05[3] | 2000 |
| 1B446 | 0.05[3] | 4000 |
| 1B374 | 0.02 | 1000 |
| 1B243a | 0.02 | 2000 |
| 1B871 | 0.02 | 2200 |
| O-35 | 0.02[3] | 2500 |
| 1B905 | 0.02 | 3000 |
| 1B7 | 0.01[3] | 1600 |
| 2A344 | 0.01 | 2500 |

TABLE 1-continued

Characterization of Class I Clones

| Clone | Relative Abundance[1] | mRNA Size[2] |
|---|---|---|
| 2A361 | 0.01 | 2500 |
| 1B338 | 0.01 | 2800 |
| O-25 | 0.01 | 4000 |

[1]Estimated relative abundance expressed as a percentage of the clones prepared. Clones that hybridize to a plurality of mRNAs are listed with each mRNA with which they hybridize.
[2]Number average of nucleotide bases.
[3]Abundance determined by filter hybridization.

TABLE 2

Characterization of Class II Clones

| Clone | Relative Abundance[1] | mRNA Size[2] |
|---|---|---|
| O-31 | 1.0 | 1400 |
| 1B372 | 1.0 | 1400 |
| 1B868 | 1.0 | 1400 |
| 1B330 | 1.0 | 2500 |
| 2A558 | 0.5 | 800 |
| 1B350 | 0.5 | 1600 |
| 1B267 | 0.5 | 1700 |
| 2A290 | 0.5 | 1900 |
| 1B360 | 0.5 | 2200 |
| O-44 | 0.2 | 600 |
| 2A384 | 0.2 | 700 |
| 1B366 | 0.2 | 1700 |
| 1B328 | 0.2 | 2000 |
| 1B330 | 0.2 | 4000 |
| 2A278 | 0.1 | 1200 |
| 2A261 | 0.1 | 1300 |
| 1B25 | 0.1 | 1300 |
| 2A346 | 0.1 | 1600 |
| 2A548 | 0.1 | 1600 |
| O-38 | 0.1 | 1700 |
| 1A188 | 0.1 | 2000 |
| 1B354 | 0.1 | 2000 |
| O-26 | 0.1 | 2500 |
| O-38 | 0.1 | 3000 |
| 1A76 | 0.1 | 3200 |
| 2A372 | 0.1 | 6000 |
| O-29 | 0.05 | 1500 |
| 1B209 | 0.05 | 2000 |
| 1B376 | 0.05 | 2000 |
| 2A388 | 0.05 | 2500 |
| 2A261 | 0.05 | 2500 |
| 1B212 | 0.05 | 2500 |
| O-42 | 0.05 | 2500 |
| O-42 | 0.05 | 3000 |
| 1B347 | 0.05 | 3000 |
| 1B227 | 0.05 | 3500 |
| O-42 | 0.05 | 3500 |
| O-42 | 0.05 | 4000 |
| 1B347 | 0.05 | 4000 |
| 1B426a | 0.05 | 4000 |
| 2A345 | 0.05 | 5000 |
| 2A550 | 0.02 | 1400 |
| 2A366 | 0.02 | 3500 |
| 2A383 | 0.01 | 1200 |
| 2A388 | 0.01 | 1200 |
| 1A74 | 0.01 | 1700 |
| 1B867 | 0.01 | 2500 |
| 1B20 | 0.01 | 3000 |
| 1B260 | 0.01 | 4000 |

[1]Estimated relative abundance expressed as a percentage of the clones prepared. Clones that hybridize to a plurality of mRNAs are listed with each mRNA with which they hybridize.
[2]Number average of nucleotide bases.

TABLE 3

Characterization of Class III Clones

| Clone | Relative Abundance[1] | mRNA Size[2] |
|---|---|---|
| O-27 | 2.0[3] | 160[4] |
| 1B224 | 2.0[3] | 160[4] |
| 2A120 | 2.0[3] | 160[4] |
| 1B308 | 2.0[3] | 160[4] |
| 1B337 | 2.0[3] | 160[4] |
| 1B208 | 2.0 | 3200 |
| 1B208 | 1.0 | 1600 |
| 1B431 | 1.0 | 2000 |
| 1B373 | 0.5 | 2400 |
| 1B426b | 0.2[3] | 1400 |
| 2A278 | 0.1 | 1500 |
| 1B207 | 0.1 | 1600 |
| 1A75 | 0.1[3] | 1700 |
| 1B213 | 0.1 | 2000 |
| 1B238 | 0.1 | 2500 |
| 1B335 | 0.1 | 3200 |
| 1B424 | 0.1 | 3500 |
| 1A216 | 0.05 | 1700 |
| O-29 | 0.05 | 2000 |
| 1A211 | 0.05 | 2500 |
| 2A563 | 0.05 | 2500 |
| 2A355 | 0.05 | 2500 |
| O-17 | 0.05 | 3000 |
| 1B319 | 0.05 | 3000 |
| 1B361 | 0.05 | 3000 |
| 2A120 | 0.05 | 3200 |
| 1B361 | 0.05 | 3300 |
| 1A168 | 0.05 | 4000 |
| O-40 | 0.05 | 4000 |
| 1A273 | 0.05 | 4500 |
| 1A186 | 0.05 | 4500 |
| 2A218 | 0.05 | 4500 |
| 1B356 | 0.05 | 4500 |
| 1B346 | 0.05 | 5000 |
| 1B205 | 0.05 | 5500 |
| 1B243b | 0.02[3] | 3000 |
| O-30 | 0.02 | 3500 |
| 2A543 | 0.02 | 5000 |
| 1B236 | 0.01[3] | 1700 |
| 1B261 | 0.01[3] | 2500 |
| 1B369 | 0.01 | 3200 |
| 1B435 | 0.01 | 3500 |
| 1B304 | 0.01 | 4000 |
| 2A355 | 0.01[3] | 4000 |
| 1B401 | 0.01 | 4000 |
| 2A302 | 0.01 | 4000 |
| 1B353 | 0.01 | 5500 |
| 1B352 | 0.01 | 6000 |
| 1B315 | 0.01 | 6000 |
| 2A347 | 0.01 | 6000 |
| 2A393 | 0.01 | 6000 |
| 2A345 | 0.01 | 8000 |
| 2A345 | 0.01 | 10000 |

[1]Estimated relative abundance expressed as a percentage of the clones prepared. Clones that hybridize to a plurality of mRNAs are listed with each mRNA with which they hybridize.
[2]Number average of nucleotide bases.
[3]Abundance determined by filter hybridization.
[4]Clones hybridize to the same, repetative nucleotide

TABLE 4

Characterization of Class IV and V Clones

|  | Class IV | Class V |
|---|---|---|
| Southern positive[1] | 19 | — |
| Southern negative[2] | — | 12 |
| Untested—36 clones[3] | 22[4] | 14[4] |
| Peculiar | — | 11 |
| Total | 41 | 37 |

[1]Clones exhibiting negative Northern blot analyses and positive Southern blot analyses.
[2]Clones exhibiting negative Northern blot analyses and negative Southern blot analyses.
[3]Clones not analyzed by Southern blot.
[4]Estimated numbers of clones in each class.

TABLE 5

Summary of Clones by Classes

| Class | Clones[1] | mRNA[2] | Percent of Total brain mRNA[3] | size avg.[4] | number avg.[5] |
|---|---|---|---|---|---|
| I | 29 (18%) | 33 | 11.95 | 1780 | 1250 |
| II | 41 (26%) | 49 | 9.55 | 2350 | 1870 |
| III | 47 (30%) | 48 (49)[6] | 6.51 (8.51)[6] | 3660 | 2640 |
| IV | 41 (26%) | (41)[7] | — | — | — |
| V | 37 | — | — | — | — |
| TOTAL | 191[8] | 130 (171)[7] | 28.01 (30.01)[6] | 2690 | 1790 |

[1]Number of clones prepared and percentage of the prepared clones.
[2]Number of mRNAs that hybridize withg the prepared clones.
[3]Percentage of total brain mRNA represented by the prepared clones.
[4]Arithmatically computed average mRNA length for each class.
[5]Sum of the product of size and abundance divided by the sum of the abundances.
[6]Value includes the ID sequence.
[7]Value includes presumed, but undetected Class IV mRNAs.
[8]Value includes four clones that fall into more than one class.

Of the four classes of clones, those clones of Clases III and IV are of import herein. Class III clones (43 of 191) hybridized to mRNA species detected in brain but not in liver or kidney, and are exemplified by clone plA75 (described in detail hereinafter). These clones correspond to 48 mRNA species that are presumed to represent the mRNAs for proteinoids expressed in the neurons and/or glia of the brain, but are not required in liver or kidney. Furthermore, some of these Class III mRNAs produce proteinoid derivatives found only in a subset of brain cells, thereby suggesting that the mRNA is expressed only in that subset of cells.

Additionally, five Class III clones hybridized to a 160 nucleotide base brain-specific, cytoplasmic, poly(A)$^+$ mRNA target, even though the cDNA insert in each clone is 500–1250 nucleotide bases long. These five clones represent precursors of brain-specific mRNAs which are a small (2–3 percent) part of the original poly(A)$^+$ cytoplasmic mRNA preparation, but contain a repetitive sequence element (ID sequence) which is also found in the small brain-specific mRNA molecule. [Sutcliffe et al., *Proc. Natl. Acad. Sci. USA*, 79, 4942–4946 (1982)).

Sixty-seven of the 191 clones failed to detect an mRNA target in the brain, liver or kidney. These clones are thought to represent either plasmids that do not contain cDNA copies of rat brain mRNA and are somehow artifactually present in the clone collection, or they could represent plasmids containing cDNA copies of relatively rare mRNAs.

The presence of rat genetic information in the plasmids was tested for by using nick translated plasmid to probe Southern blots of rat DNA [Southern, *J. Mol. Biol.*, 98, 503–517 (1975)] to distinguish between those possibilities.

Of 31 clones selected at random from the 67 Northern blot negative clones, 19 (61%) hybridized to restriction fragments in Southern blots of rat liver DNA suggesting that those 19 clones did correspond to rare mRNAs transcribed from rat genes.

Because the 31 clones were selected randomly from the 67 Northern blot negative clones, it is presumed that 61%, or 22 clones of the remaining 36 untested clones also correspond to rare mRNAs transcribed from rat genes. Thus, a total of 41 clones correspond to rare brain mRNAs and those 41 clones comprise the Class IV clones.

The remaining 26 Northern blot-negative clones are believed to be artifacts of cloning and have been assigned to a Class V (Table 4). Class V also includes 11 clones that showed peculiar hybridization patterns and could not be classified along with the clones of Classes I–IV. Usually, the peculiar hybridization patterns were smears with brain, liver and kidney mRNAs showing no discrete bands. Presumably, the smeared hybridization pattern is due to hybridization of the poly(T) sequence in the plasmid to the poly(A) tails present in the mRNAs of all size classes and all three tissue mRNA preparations.

In sum, a total of 191 clones have been examined of which 154 correspond to 171 mRNAs (including the 41 presumed Class IV mRNAs). Together, these clones account for more than 28 percent of the total cytoplasmic poly(A)$^+$ mRNA (by mass) of the rat brain. An additonal 2 percent of the poly(A)$^+$ mRNA is accounted for by the brain-specific 160 nucleotide base mRNA. The fraction of clones falling into each class is indicated in Table 5, above. The largest fraction is that of the brain-specific Class III clones (30%). Presuming that all or most of the Class IV clones also correspond to rare brain-specific mRNAs, then more than half of the clones appear to correspond to mRNAs uniquely expressed in the brain.

The arithmetic and number average sizes of the mRNAs listed in Tables 1–3 were computed for each class and for overall brain mRNAs (Table 5). The arithmetic average represents the average length of the mRNAs assessed by the probes used. The number average reflects the average length of the population of mRNAs represented by the clones; it is weighted by the abundances of each particular mRNA and is the appropriate figure to compare with measurements of the average length of a heterogenous mixture of mRNA molecules such as those used in solution hybridization determinations of mRNA complexity.

The overall number average length of brain mRNAs detected by the clones (Classes I–III) is 1790 nucleotide bases, a figure compatible with the measurements of previous authors, which ranged from 1400–1900 nucleotide bases. [See Bantle et al., *Cell*, 8, 139–150 (1976); Hastie et al., *Cell*, 9, 761–774 (1976); and Gros et al., In *Molecular Genetic Neuroscience*, Schmitt, Bird and Bloom, eds., Raven Press, New York, 335–347 (1982).]

The arithmetic average length of the set of Class III clones is considerably larger, 2640 nucleotide bases. The length of the Class IV clones is presumed to be still larger, averaging about 4960 bases. This indicates that the most prevelant mRNAs in the brain tend to be smaller than the rarer mRNAs. The same conclusion holds when the two averages are computed for mRNAs of each individual class, namely the more prevalant mRNAs tend to be shorter than the rarer mRNAs. Surprisingly, Class III mRNAs are, on average, more than twice as large as those expressed equally in other tissues.

The abundances of the mRNAs corresponding to the clones of Table 1–3 were not measured directly for each clone. Rather, the abundance of the mRNA corresponding to 11 clones was measured directly, and the relative abundances of the other clones were based upon a comparison of hybridization probe-specific activities, autoradiographic exposure times and relative band intensities to the directly measured cases. The resulting, estimated abundances were rounded off so that each mRNA was placed into one of several discrete abundance classes. Hence, the abundance estimates are believed to be accurate to a factor of about two. Furthermore, when the estimates fell below about 0.01 percent, those estimates were rounded upwardly to about 0.01 percent.

Several of the 47 clones of Class III were selected for more detailed study as is described hereinafter. For each, the approach was to determine its nucleotide sequence, followed by the use of purified, single end-labeled restriction fragments from the clone to determine the sense strand of the corresponding mRNA. Potential triplet open reading frames (orfs) were then decoded into amino acid residue sequences using the well-known genetic code. The resulting hypothetical protein sequences were thereafter compared by computer analysis to the collection of known protein sequences to detect possible identities or similarities with previously known proteins. Finally, the open reading frames which appeared most likely to be translated by the cell into proteinoids were selected, and short polypeptides corresponding to regions from these hypothetical amino acid residue sequences were chemically synthesized and used as immunogens in rabbits. The resulting antisera were used to detect proteinoids or derivatives thereof in fixed brain sections using immunocytochemical techniques.

II. CHARACTERIZATION OF EXEMPLARY BRAIN-SPECIFIC CLONES

Four brain-specific clones of Class III are described hereinafter as exemplary. These clones are designated plA75, plB236, plB208 and p0-40. The general properties of these clones are summarized in Table 6 hereinafter.

The clone insert sizes of 1126, 1500, 978 and 1200 bases respectively were derived from the nucleotide sequence of each insert. The mRNA sizes were estimated from the mobility on agarose gels of the brain-specific mRNA target to which each clone hybridized in a Northern blot. The mRNA abundance was determined by measuring the amount of broken, $^{32}$P-labeled poly(A)$^+$ mRNA which hybridized to excess plasmid DNA.

In brief, these four DNA clones represent mRNA molecules of 1600–4000 nucleotide bases, each of which is present at a concentration ranging roughly from about 0.01 percent to about 2 percent of total brain mRNA. Based upon the sensitivity of the blot utilized herein, it is estimated that the level of the corresponding mRNA in liver or kidney is less than one copy per cell, assumming about 200,000 mRNA molecules per cell. Thus, the mRNAs of the four clones and those of Classes III and IV are substantially absent from other body tissues such as liver and kidney, or put differently, the mRNAs are present substantially only in brain cell tissues.

As the brain is comprised of many distinguishable structures and cell types, cDNA clones were used as probes for hybridization to mRNA preparations of the brain from seven sub-regions (cortex, olfactory bulb, hippocampus, hypothalamus, caudate nucleus, cerebellum and pons/hind brain) to define any further regional specificity. The clones were also hybridized to mRNA from tumors of neural origin [a mouse neuroblastoma, rat pheochromocytoma (PC12)

and a rat glioma] to determine any cellular specificity. These results are discussed later and are also summarized in Table 6.

TABLE 6

Properties of Clones p1A75, p1B236, p1B208 and pO-40

| Clone | Insert[1] | mRNA Length[2] | mRNA Abundance[3] | mRNA Location[4] |
|---|---|---|---|---|
| P1A75 | 1126 | 1700 | 0.1 | all brain, PC12 cells |
| p1B236 | 1500 | 1700 | 0.01 | mid brain, hind brain |
| p1B236 | 1500 | 3200 | 2 | hind, mid and forebrain |
| p1B208 | 978 | 1600 | 1 | glioma cells |
| pO-40 | 1200 | 4000 | 0.05 | all brain |

[1]Length of nucleotide sequence of each clone inserted into the plasmid.
[2]Number average length in nucleotide bases.
[3]Estimated abundance as a percentage of total brain mRNA.
[4]Location in the brain at which the mRNA is present.

III. THE CLONES

A. Clone p1A75

The p1A75 cDNA clone hybridized to a 1700 nucleotide base pair mRNA present at about 0.1 percent of total rat brain cytoplasmic poly(A)$^+$ mRNA and is not present in either liver or kidney poly(A)$^+$ mRNAs as can be seen from examination of FIG. 1A. The mRNA corresponding to the p1A75 clone is expressed about equally in all seven dissected regions of the brain as can be seen from a examination of FIG. 1B. The failure to hybridize to liver and kidney mRNA preparations is not due to degradation of mRNAs from those tissues because another cDNA clone (p1B15) whose mRNA is not tissue regulated, hybridized as well to the same mRNA preparations of those non-neural tissues as it does to the brain (data not illustrated).

In the regional preparations of brain mRNA, the non-regulated mRNA hybridizing to p1B15 acts as an internal normalizer to show that approximately equal amounts of mRNA were loaded in each gel lane. Hence, different levels of hybridization represent real differences in the concentration of the p1A75 mRNA in the various tissues. The apparent enrichment of the p1A75 mRNA in cerebellum is accompanied by an equal increase in the control p1B15 signal, and so must reflect more total mRNA applied to the gel rather than an increase in p1A75 mRNA concentration.

The p1A75 mRNA is expressed in PC12 cells but not in glioma or neuroblastoma as is seen in FIG. 1A. Therefore p1A75 is likely to correspond to mRNA that translates to a proteinoid produced in neurons and possibly neuroendocrine cells but not in glia.

Two restriction fragments from each cDNA insert were prepared to determine the coding strand of the 1126 nucleotide base p1A75 sequence (FIG. 1C). Each fragment was $^{32}$P-labeled on one of the two alternative 5' ends so that a hybridization probe for each of the two possible mRNA orientations was prepared as is shown in FIG. 1D.

One probe hybridized to the 1700 nucleotide mRNA on a Northern blot, showing that it was labeled on the strand complimentary to the mRNA; the other probe did not hybridize as is shown in FIG. 2E. This result demonstrates that the sequence shown in FIG. 1C corresponds to the coding strand of the mRNA. Thus, clone p1A75 is a 1126 residue sequence of a portion of the sense strand of a brain-specific 1700 nucleotide base mRNA that represents about 0.1 percent of total brain mRNA.

Figure 1D:
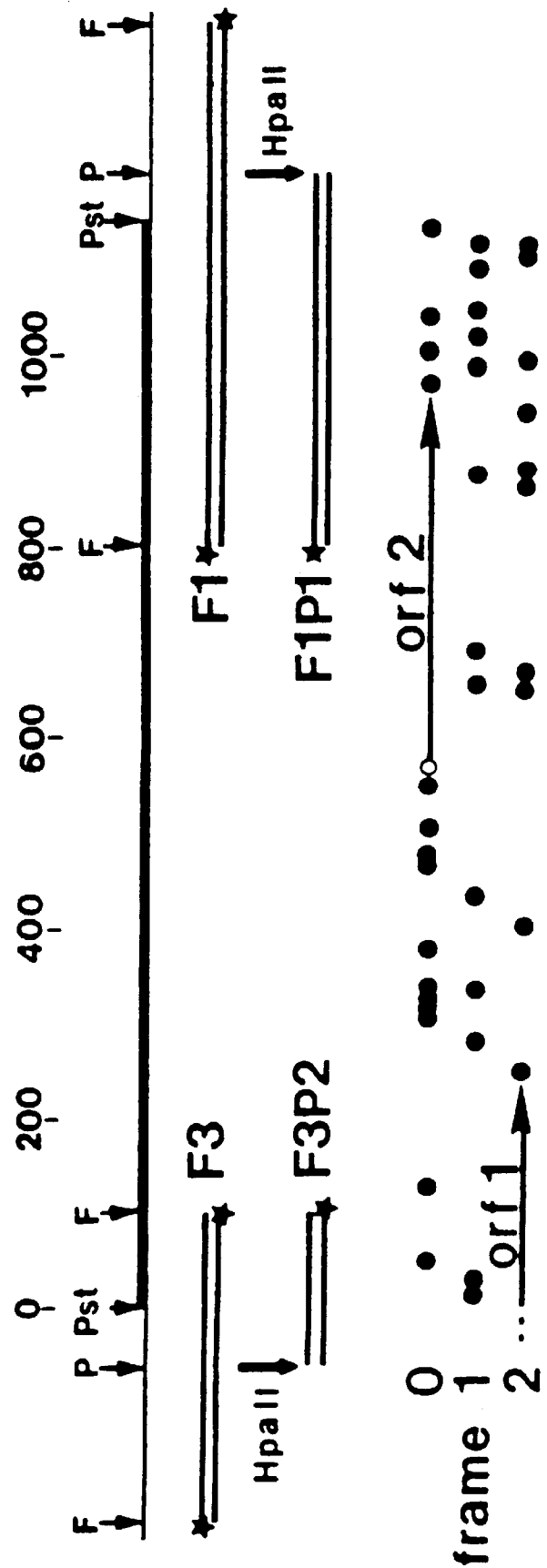
FIG. 1D illustrates a determination of the sense strand and open reading frames of the plA75 cDNA clone. Clone plA75 is represented at the top showing the cDNA insert (thick line) in the same orientation as in FIG. 1C in plasmid pBR322 (thin line). The cleavage sites of the following restriction enzymes are indicated; Hpa II (P), Hinf I (F) and Pst I. Illustrated below are both strands of the restriction fragments (referred to as F1, F1P1, F3 and F3P2) used to determine the sense strand of the cDNA clone. The $^{32}$P-labeled 5' termini are indicated by an asterisk (*) The positions of TGA, TAA or TAG termination codons in each of the three possible reading frames are illustrated at the bottom by darkened dots (●). Also illustrated are the two largest orfs. The position of the ATG initiation codon of orf 2 is illustrated by an open dot (o).

The nucleotide sequence was then scanned for translation initiator triplets (ATG, GTG) and terminator triplets (TGA, TAA, TAG), as shown in FIG. 1D, to determine the nature of the protein that could be translated from this mRNA. The well known genetic code was used to decode any sizable possible open reading frames (orfs) into hypothetical proteinoids.

There are only two such large orfs in the p1A75 sequence, both of which have been decoded into proteinoid sequences from the sense strand of the cDNA sequence as is shown in FIG. 1C. One possible frame (orf 1) is unbounded on the 5' end and extends for 82 triplets until reaching a terminator. The other frame (orf 2) is 119 triplets in length, and is completely contained within the p1A75 sequence.

Since it is not known from the sequence itself exactly how the 1126 nucleotide bases of cDNA of clone p1A75 are aligned within the 1700 nucleotide bases of the mRNA, e.g. 5', middle or 3', orf 1 could potentially be translated by the cell into a proteinoid of up to about 30 kilodaltons (30K daltons) while orf 2 potentially translates to a proteinoid which must be about 13K daltons. A computer search of each of the two hypothetical sequences, in overlapping segments of 30 residues revealed no homologies with any known protein sequences, Dayhoff et al., *PSO Version 4*, Apr. 30, 1982, National Biomedical Research Foundation, Georgetown University Medical Center (hereinafter referred to as the "Dayhoff atlas").

Two approaches were used to determine if either of the hypothetical orf sequences corresponds to a brain-specific proteinoid. Denatured p1A75 DNA was bound to nitrocellulose filters. The filters so prepared were then used to purify complimentary mRNA by hybridization with total brain poly(A)$^+$ mRNA. After extensive washing of the filter, the bound mRNA was released by boiling and used to program in vitro protein synthesis (hybrid-release translation) as described by Cleveland et al. *Cell,* 20, 95–105 (1980).

Figure 2A:
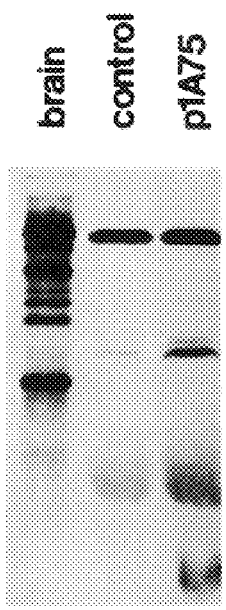
FIG. 2A is a photograph of an autoradiogram illustrating a hydribization translation assay of clone plA75. Poly (A)$^+$ mRNA from rat brain and mRNAs which hybridized to control or plA75 filters were translated in vitro using rabbit reticulocyte lysate, and $^{35}$S-methionine-labeled products were fractionated by electrophoresis on 12.5 percent sodium dodecyl sulfate polyacrylamide gel (SDS-PAGE). The arrow indicates a band of approximately 25 kilodaltons (25K daltons) which appears with plA75 hybridizable mRNA but not in the control. The molecular weight estimate is based on results from comparable gels as no markers were run with these samples.

The purified mRNA stimulated the synthesis of a proteinoid with a gel mobility of approximately 25K daltons which was not present in control reactions (FIG. 2A). Unpurified brain poly(A)$^+$ mRNA programmed into synthesis of many proteinoids. From these determinations, the size of this molecule (25K daltons) suggested that orf 1 is likely to be translated into the product of the p1A75 mRNA because orf 2 and any other possibility was too small.

Two 13-residue synthetic polypeptides, P1 and P2 corresponding to two amino acid residue sequences within orf 1 were chemically synthesized to detect the putative product of the p1A75 mRNA translation. The polypeptides underlined in FIG. 1C, were chosen so as to contain proline residues and charged residues, using the rules discussed by Sutcliffe et al., *Science,* 219, 660–666 (1983). Those polypeptides were then coupled to a variety of carriers as discussed in the Materials and Methods Section. A synthetic polypeptide, denominated P3, was also synthesized from orf 2. Synthetic polypeptides P1, P2 and P3 are hereinafter sometimes referred to as P1, P2 and P3, without reference to their being synthetic polypeptides.

The amino acid residue sequences of the three polypeptides were compared to the Dayhoff atlas, above, by computer database search to preclude the possibility that at reasonable concentrations, antisera to any of these three polypeptides would specifically interact with any protein of a known sequence. None of the three polypeptides were found to have a close homolog.

Antisera to the polypeptide-carrier conjugates were raised in rabbits. The sera were shown to react strongly with the appropriate polypeptides by ELISA following the procedures of Green et al., *Cell,* 28, 477–487 (1982).

Figure 2B:
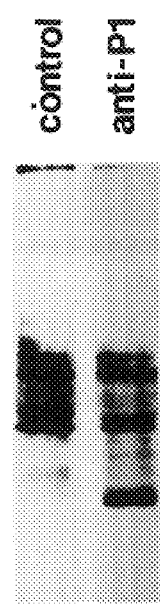
FIG. 2B is a photograph of an autoradiogram illustrating a 5 to 12.5 percent gradient SDS-PAGE analysis of immunoprecipitates of $^{35}$S-methionine-labeled products from metabolically labeled rat pheochromocytoma (PC12) cells using antipeptide antibodies (either plA75 anti-Pl or control antibodies). The arrow indicates an approximately 28K dalton protein (estimates from markers run in adjacent lane) was precipitated by anti-Pl serum.

The antisera were then used to probe extracts of $^{35}$S-methionine labeled PC12 cells which produce P1A75 mRNA. Thereafter, antisera to synthetic polypeptide P1 was found to react with a proteinoid with a slightly diffuse gel mobility of about 28K daltons (FIG. 2B). Anti-synthetic polypeptide P2 serum showed a lower reactivity against a proteinoid with the same gel mobility, but anti-synthetic polypeptide P3 sera were unreactive (data not shown).

Figure 2C:
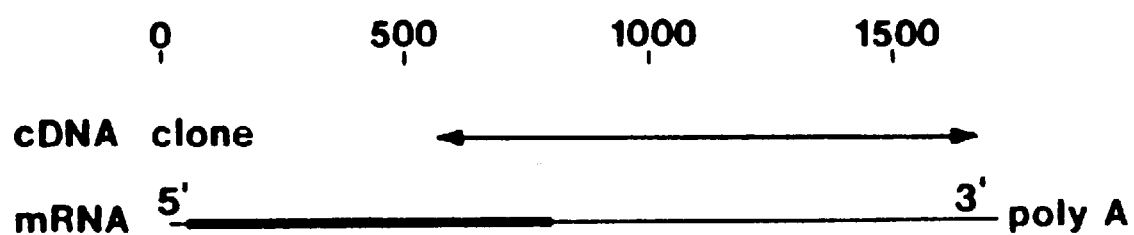
FIG. 2C illustrates the alignment of the pIA75 cDNA clone with its corresponding mRNA showing putative locations of coding (thick line) and non-coding regions (thin line).

Orf 1, therefore, is the proteinoid coding frame of the mRNA corresponding to plA75. Since only 82 triplets of orf 1 are at the 5' end the cDNA sequence, and orf 1 is translated to part of 28K dalton product, plA75 must represent a 3' region of a corresponding mature mRNA (FIG. 2C). There is, therefore, a long 3' untranslated region on this mRNA exceeding about 800 nucleotides. Approximately 450 nucleotides of the 5' prime coding sequence are therefore lacking.

To determine in which cells in the brain the plA75 orf proteinoid is expressed, thin, fixed sections of rat brain were reacted with anti-P1, anti-P2 and anti-P3 sera. The sections were washed, and antibody-antigen (receptor-ligand) complexes were visualized with horseradish peroxidase (HRP)-coupled anti-rabbit immunoglobulin.

Figure 3A:
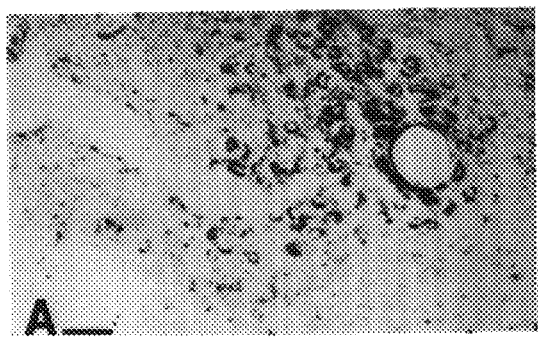
FIG. 3A is a photomicrograph illustrating a group of neurons in the paraventricular nucleus of the hypothalamus that show intense staining using anti-P1 antisera. The bar equals 50 microns.
Figure 3B:
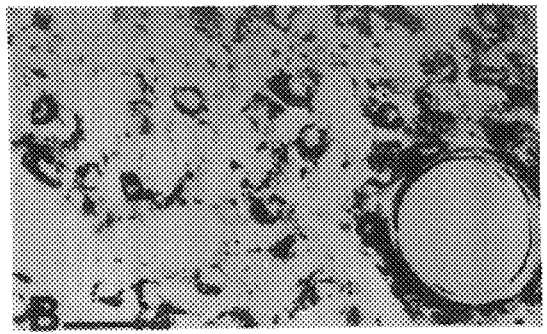
FIG. 3B is an enlarged view of the cells in FIG. 3A showing cytoplasmic granules.
Figure 3C:
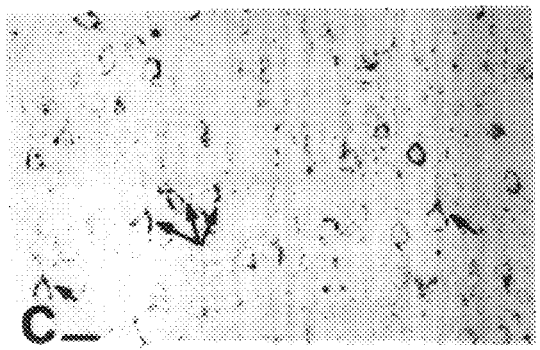
FIG. 3C is a photomicrograph of neurons and dendritic processes in the subiculum stained using anti-P1 antibodies and showing frequent concentrations of immunoreactivity in the dendritic pole of the cells (arrows). The bar equals 50 microns.

One antiserum against synthetic polypeptide P1 reacted with the cell bodies of some neurons located throughout the brain (FIGS. 3A–3C), including many large neurons such as cortical pyramidal cells. The reactivities appear to be cytoplasmic and have a granular appearance. Frequently, the granules are concentrated in the dendritic pole of the cell and are often observed in the dendrites themselves (FIG. 3C). The reacting cell bodies were found in the cerebellum, deep cerebellar nuclei, hypothalamus, superior colliculus, subiculum and cerebral cortex.

Figure 3D:
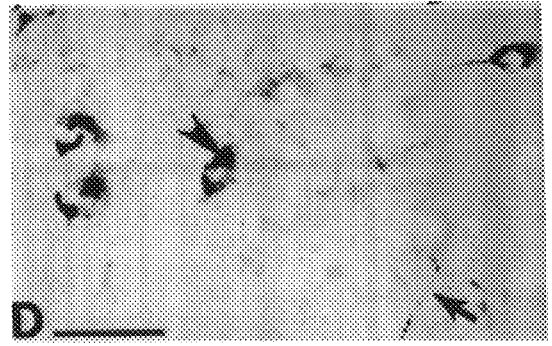
FIG. 3D is a photomicrograph illustrating hypothalamic cell bodies stained using anti-P2 antibodies. A stained varicose fiber is also indicated. The bar equals 50 microns.

Anti-P2 sera gave a similar pattern of cytoplasmic staining, but it was limited to a small group of cells in the hypothalamus (FIG. 3D). Those data, together with the anti-P1 staining pattern, are interpreted to mean that the proteinoid in the hypothalamus is somehow more immunoreactive, and that the anti-P2 sera are weaker as noted for the immunoprecipitation of PC12 extracts.

The anti-P2 immunoreactivity was blocked by preincubation of the antiserum with synthetic polypeptide P2. The reactivity of the anti-P1 serum could not be blocked with synthetic polypeptide P1, with the P1-thyroglobulin conjugate to which the antiserum was raised or with thyroglobulin alone.

Since the distinct cytoplasmic granular nature of the staining is the same throughout the brain and looks similar with the antisera to the two polypeptides in the hypothalimus, and since both antiser react with proteinoids of the same size in extracts of PC12 cells, both anti-P1 and anti-P2 sera are probably reacting with the same proteinoid or derivative thereof in the brain; i.e., the 28K dalton product of the plA75 mRNA seen in the PC12 extracts.

Antibodies against synthetic polypeptide P3 were not reactive in any brain region. That result is consistent with the conclusion that orf 2 is not the true coding region of plA75.

The distribution of anti-P1 and anti-P2 immunoreactivity is in general accord with the regional localization of plA75 mRNA as shown in FIG. 1B, the reactive cell bodies being located throughout the brain. The staining was not observed in all cells, but was limited to a subset of neurons which appear to be morphologically related: many of the reactive cells are large projection neurons such as pyramidal cells. The cytoplasmic location of the reactive proteinoids within the cells, and the granular appearance and polar orientation of the immune reaction, suggest that this proteinoid or derivative thereof could be involved in the synthesis or directional export of proteinacious or materials destined for dendrites, or it could be a component of cytoplasmic organelles, such as mitochondria. These results therefore document the discovery of a 28K dalton proteinoid that is expressed selectively in roughly homologous neurons and whose carboxy-terminal 82 amino acid residues are now known.

The antibodies to synthetic polypeptides P1 and P2 or idiotype containing polyamides made therefrom are thus useful receptors for the study of the synthesis of the 28K dalton protein in PC12 or other nerve cells, and are useful to define the location of that proteinoid or its derivative in brain cell tissue by more detailed immunocytochemistry and electron microscope studies. These specific receptors (antibodies or idiotype-containing polyamides made therefrom) can also facilitate the purification of the endogenous brain cell tissue products by conventional biochemical means for further sequence determination and assay of potential function. The organelle-like location of the proteinoid within cells suggests an involvement in secretory, transport or mitochondrial functions, and gives important clues as to how the determination of the function of this proteinoid may be approached.

The amino acid residue sequence of synthetic polypeptides P1, P2 and P3 are as represented by the formulas below, from left to right and in the direction from amino-terminus to carboxy-terminus, using conventional single letter code for amino acid residues:

| P1 | CIPEGLESYYTEQ; |
| P2 | RSVSPWMSVLSEE; and |
| P3 | CRPYPIHRVTPRS. |

B. Clone plB236

Figures 4A, 4B:
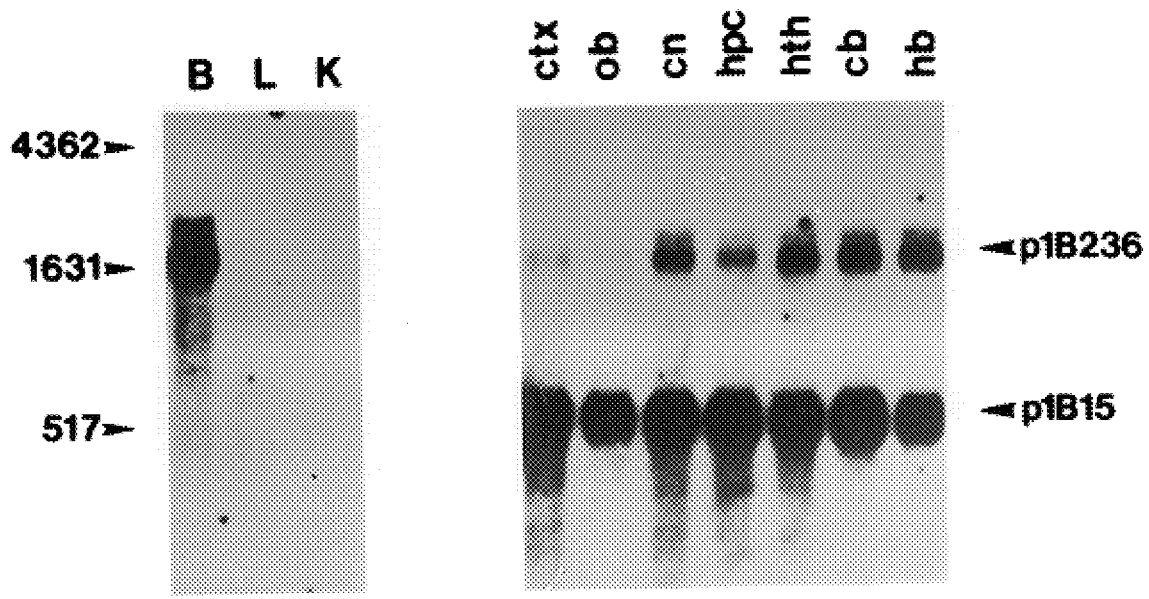
FIG. 4A is a photograph of the autoradiogram illustrating Northern blot analysis of the tissue distribution of pIB236 mRNA. Details are as described in FIG. 1A.
FIG. 4B is a photograph of an autoradiogram illustrating Northern blot analysis of the regional distribution of pIB236 mRNA and pIB15 mRNA in rat brain. Details are as described in FIG. 1B.

The plB236 cDNA clone hybridizes to a brain-specific 1700 nucleotide mRNA representing 0.01 percent of total brain mRNA (FIG. 4A) . This mRNA is distributed in low amounts in cortex and olfactory regions, and in larger amounts in mid and hind brain regions (FIG. 4B). This mRNA is not expressed in any of the three tumors thus far tested, nor is it expressed in gut, lung, heart or skeletal muscle.

Figure 4E:
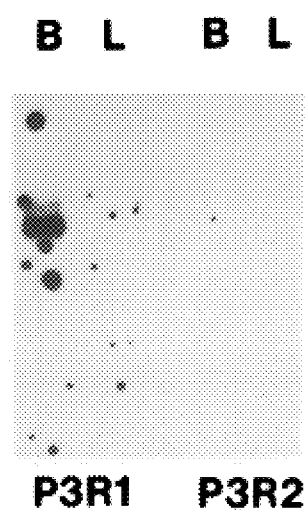
FIG. 4E is a photograph of an autoradiogram illustrating detection of pIB236 mRNA by single end-labeled restriction fragments prepared as indicated in FIG. 4D. Details are as described in FIG. 1E.
Figure 4C-1:
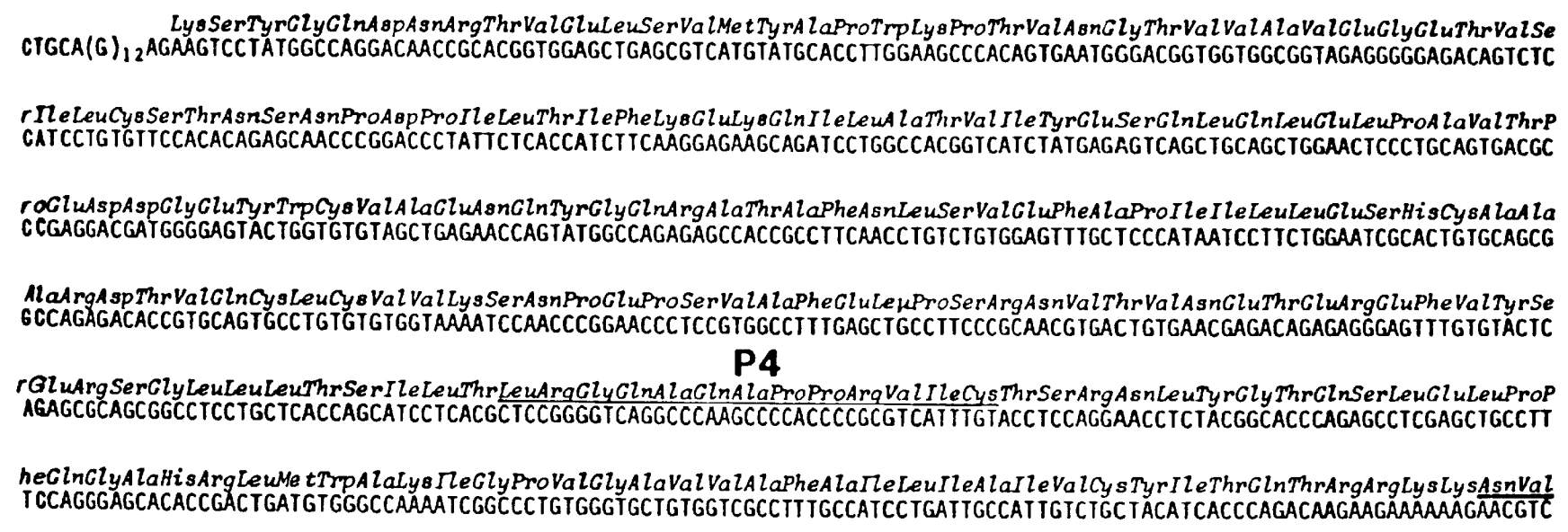
Figure 4D:
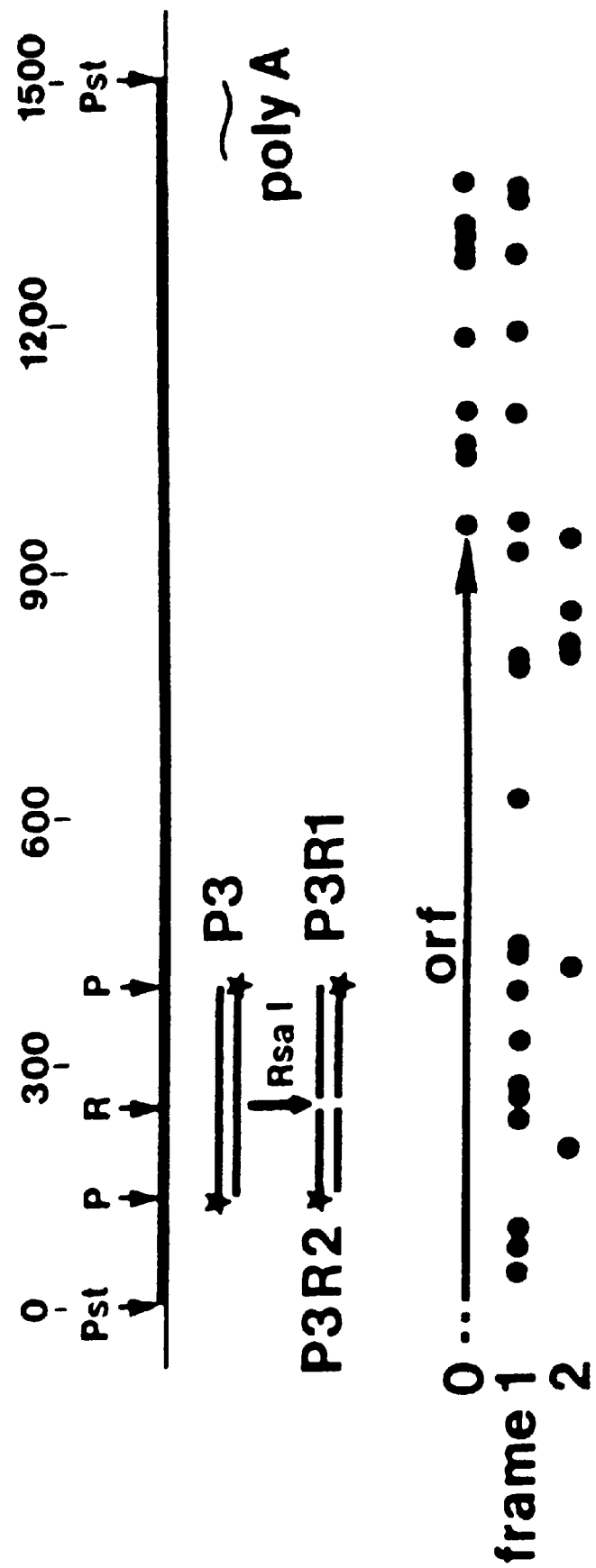
FIG. 4D illustrates the determination of the sense strand and open reading frame of clone pIB236. Details are as described in FIG. 1B. R is an abbreviation for restriction endonuclease Rsa I.

The approximately 1500 nucleotide sequence of the strand depicted in FIG. 4C was shown to be the sense of strand of the mRNA by a determination analogous to that described above for clone plA75, utilizing single $^{32}$P-end-labeled restriction fragments of opposite orientations to probe a Northern blot as is shown in FIGS. 4D and 4E. In addition, since the plB236 sense strand sequence terminates with a poly(A) stretch of over 100 bases, the exact number being uncountable on the sequence gels, and contains a variant poly(A) addition sequence (AACAAA) 17 nucleotide bases upstream, it appears quite certain that this is the proteinoid coding strand.

After scanning the sequence for terminator triplets (FIG. 4D) , it is clear that the long orf bounded at the 5' end of the clone and extending for almost 1000 nucleotides must be the coding frame. This leaves 450 nucleotides of the 3' non-coding information.

The putative amino acid sequence of 318 residues (indicated above the nucleotide sequence of FIG. 4C) although unbounded at its amino-terminus, cannot be too much larger, for the full length of the mRNA is estimated to be only about 200 nucleotides larger than the plB236 cDNA insert. The 318 residue proteinoid sequence was compared by computer analysis in overlapping sequences of 30 residues each to the proteins of the Dayhoff atlas, above, but no notable homologies were detected.

The plB236 DNA was bound to nitrocellulose filters, and complementary mRNA was purified and translated in vitro as described for clone plA75. However, no specific translation product was observed. This was not altogether surprising since plB236 hybridizes to a rarer mRNA than the mRNA corresponding to plA75.

Figure 5:
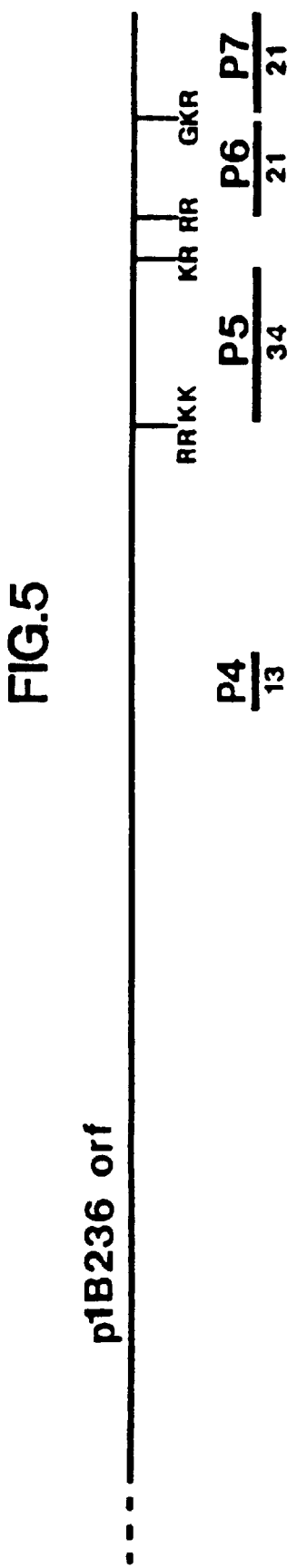
FIG. 5 illustrates the pIB236 open reading frame. Shown are the positions of potential polypeptide processing sites at pairs of basic amino acids (K=lysine, R=arginine); the positions of the synthesized polypeptides P4, P5, P6 and P7 (the numbers of the amino acids in each are shown underneath); and the position of the carboxy-terminal glycine (G) which may be involved in the amidation of polypeptide P6.

The 318 amino acid sequence of the probable plB236 coding frame is similar to the that of known precursor of pharmacologically active neuropeptides and is shown schematically in FIG. 5. The carboxy-terminal region contains a series of tandem basic amino acids: arg-arg, lys-arg, and arg-arg-lys-lys. Such pairs of basic amino acid residues are proteolytic cleavage sites in the precursors for many neuropeptides or hormones such as proopiomelanocortin [Nakanishi et al., Nature, 278, 423–427 (1979)] calcitonin [Amara et al., Nature, 295, 240–244 (1982)] and the precursors for vasopressin/neurophysin [Land et al., Nature 298, 299–303 (1982)] and beta-neoendorphin/dynorphin Kakidani et al., Nature, 298, 245–249 (1982)]. Furthermore, in most of these examples, the active polypeptide sequences are located in the carboxy-terminal end of the precursor, very similar to that which is seen herein.

Three (P5, P6 and P7) of five polypeptides from the regions demarcated by the pairs of basic residues, shown as bars in FIG. 5 and underlined in FIG. 4C, were prepared synthetically since it was desirous to identify the plB236 proteinoid in rat brain by use of antisera raised to the synthetic polypeptides. Those polypeptides used as immunogens for the preparation of antisera were themselves also studied to ascertain the pharmacological activities. Synthetic polypeptides denominated P4-P8 are also sometimes referred to herein without the descriptive phrase "synthetic polypeptide."

Synthetic polypeptide P6 is particularly noteworthy as its carboxy-terminal residue is glycine. Several carboxy-terminally amidated polypeptides such as vasopressin (Land et al., above), calcitonin (Amara et al., above) and alpha-MSH (Nakanishi et al., above), are cleaved from precursors at GlyArgArg sequences, and transamidated, the glycine being eliminated to leave the newly formed carboxy-terminal residue in the amide rather than carboxy form. Synthetic polypeptide P6 is therefore a candidate for such a post translational modification, and as such provides further structural indication that its sequence may represent a neuropeptide precursor.

Synthetic polypeptides translated from mRNAs present substantially only in brain cell tissues that translate to a proteinoid or proteinoid derivative containing a GlyArgArg sequence that may be cellularly transformed by the above cleavage-transamination reaction to provide a carboxy-terminal amide group on the residue to the amino-terminal side of the GlyArgArg sequence; i.e., adjacent to the Gly residue, are also particularly contemplated herein. Such synthetic polypeptides consequently do not contain a carboxy-terminal glycine as do P6 and P8. Rather, the carboxy-terminal glycine residue is deleted, and the carboxy-terminal amino acid residue contains an amide group, denominated herein as an amino acid residue one-letter symbol followed by "—$NH_2$". Such synthetic polypeptides are exemplified by synthetic polypeptides P9 and P10 whose amino acid residue sequences are shown hereinafter.

As in the study of clone plA75, the synthetic polypeptides were coupled to carriers to form conjugates, and the conjugates were used to immunize rabbits. The resulting synthetic polypeptide-reactive antisera were used for immunocytochemical studies. The details of this work are as reported in the Materials and Methods Section hereinafter.

Indirect immunoperoxidase staining, as discussed above, was performed with antisera raised against synthetic polypeptides P4, P5, P6 and P7. Staining with antisera raised against synthetic polypeptide P4 was consistently negative. However, four sera raised against P5 and two sera raised against P6 and one serum raised against P7 have given similar overall patterns of immunoreactivity in rat brain.

Figure 6A:
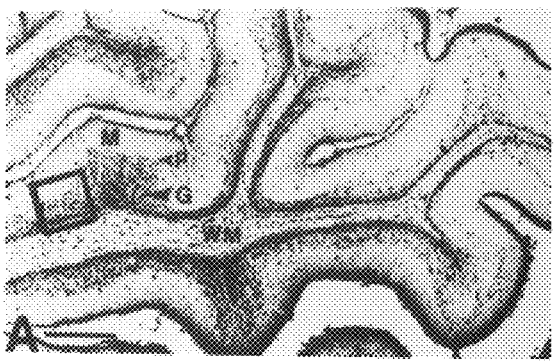
In FIGS. 6A–6C and 6E–6Ha, all sections are also counterstained with Richardson's stain.

Immunoreactivity was found in a fiber system distributed throughout the brain, with distinctive patterns most extensively revealed in pons, cerebellum (FIG. 6A), hypothalamus and regions of a hippocampus and neocortex. In cerebellum, hippocampus and neocortex, thick variocose fibers are seen in direct relationship to the perikarya (cell bodies) of the principal output cells of each region.

Figure 6B:
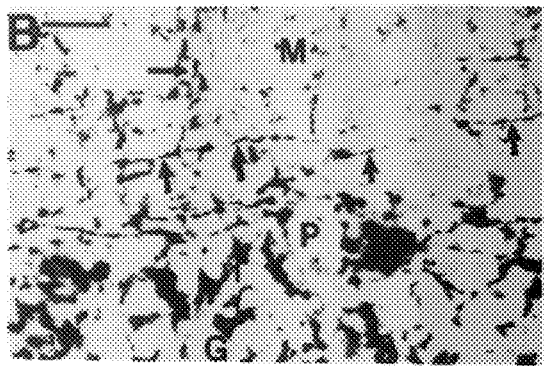
Figure 6C:
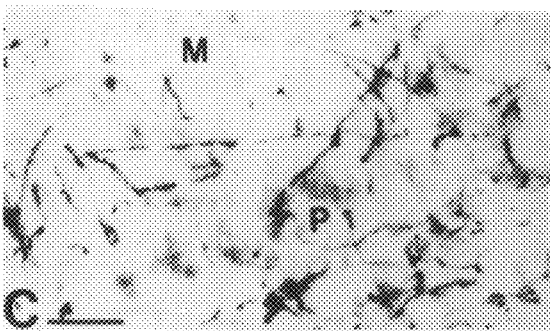
Figure 6D:
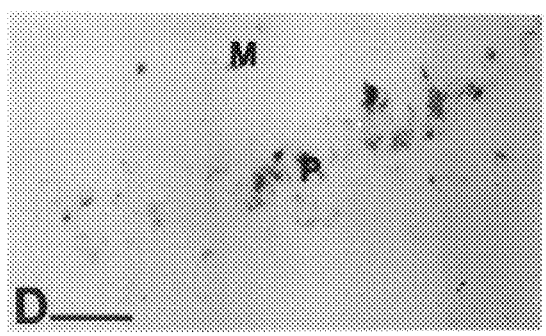
FIG. 6D is a photomicrograph illustrating a similar view as in FIG. 6C but with anti-P5 antibody preabsorbed with polypeptide P5. Unreactive neurons are counterstained with cresyl violet. The bar equals 50 microns.
Figure 6E:
Figure 6F:
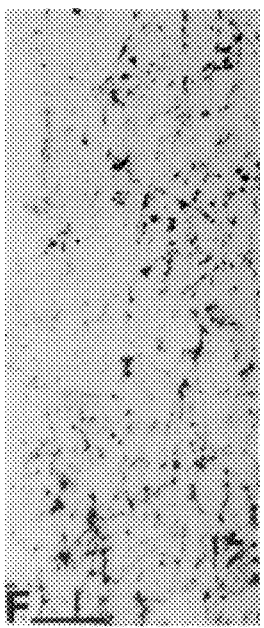
Figure 6G:
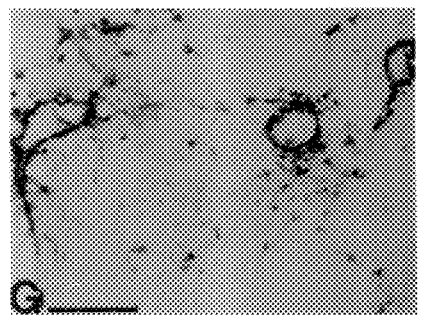

In the hippocampus and cerebellum, the axon-like processes stained by antisera to P5 thickened, surrounding (and probably making synapses on) the cell body and proximal dendrites of the $CA_3$ pyramidal neurons (FIG. 6C) and Purkinje neurons, respectively. Nerve terminal-like process are also found in the cerebellum within the the granule cell layer (FIGS. 6A and 6B) and surrounding (and probably making synapses on) a sizable fraction of the large neurons of the deep cerebellar nuclei (FIG. 6G). Within the neocortex, immunoreactivity is most intense in the posterior cingulate cortex, with radially-directed axon-like staining in layers 3, 4, 5 and with tangentially directed fibers resembling a terminal field in layer 1 (FIG. 6E). A similar pattern is seen in certain regions of the somatosensory cortex where staining is in radially directed fibers spanning layers 2–5, and again tangentially directed in the outermost zone of layer one.

With antisera to P6, staining in neocortex is similar in all respects (FIG. 6F), except that the staining is fainter, and is virtually absent in the tangentially arranged structures of layer 1. Staining with antiserum to P7 is indistinguishable from staining with antiserum to P5. Additionally, fiber staining is also observed within axons of the heavily myelinated tracts of the fornix, the corpus striatum, and the lateral olfactory tract, as well as in the hypothalamic tract and the striamedullaris. However, with the exception of the some very faintly reactive cell bodies in the ventromedial and basal arcuate regions of the hypothalamus, immunoreactive cell bodies are difficult to visualize in fixed brains of untreated rats.

To improve detection of immunoreactivity within cell bodies, rats were treated with colchicine, which blocks axonal transport from neuronal cell bodies to terminals, causing transported material to accumulate in the cell bodies. This treatment facilitates immunodetection of the material at its site of synthesis.

Figure 6H:
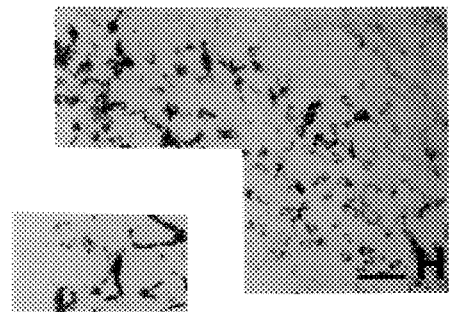

In colchicine treated rats, fiber-like staining with antisera to P5 was considerably reduced; this reduction was most obvious within the granule and molecular layers of the cerebellar cortex and within layer 1 of the cingulate and neocortex. Although fiber staining was reduced, distinctive immunoreactive cell bodies were thus observed in which cytoplasm, but not the nucleus became immunoreactive. Such immunoreactive cell bodies (FIG. 6H) were clearly discerned in the brain stem (in the medial nucleus of the trapezoid body, the ventro pontine tagmental area, and the nuclei of the pontine raphe system) and more clearly than in untreated rats within the lateral ventro-medial and basoar-cuate nuclei of the hypothalamus and the caudate nucleus. The distribution of these immunoreactive cell bodies is consistent with the regional localization of plB236 mRNA.

All immunoreactivity with the antiserum which was used for the majority of the studies on normal and colchicine-treated rats was identical at dilutions of from 1:500 to 1:10000. When the antiserum at a 1:1000 dilution was preabsorbed with synthetic polypeptide P5, all immunoreactivity was abolished (FIG. 6D). Similar absorptions of this antiserum with synthetic polypeptides P4 and P6 had no effect on the staining pattern or intensity. Similarly, the anti-synthetic polypeptide P6 reactivity was specifically blocked with synthetic polypeptide P6, and the anti-P7 reactivity was blocked by preincubation with synthetic polypeptide P7. Tnus, based on the coincident pattern of immunoreactivity of antisera to the three synthetic polypeptides, the staining was specific for the plB236 mRNA product.

The selective and specific staining patterns observed with several antisera to synthetic polypeptides P5, P6 or P7 of the plB236 orf deduced from its sequence strongly suggest that an extensive system of neurons with a reproducible pattern of circuitry relationships may contain this proteinoid. The appearance of immunoreactive cell bodies in colchicine-treated rats, together with a simultaneous loss of fiber staining, further supports the view that the immunoreactive material is synthesized in certain neuronal cell bodies and transported nerve terminals.

Extracts from rat brain cell tissue homogenates were analyzed by Western blot as generally described in Towbin et al., *Proc. Natl. Acad. Sci. USA*, 76, 4350–4354 (1979). Sera raised to P5, P6 and P7 showed coincident, peptide-blockable reactivity for each serum.

The reactive proteinoid had a diffuse gel mobility of 100K daltons. This proteinoid is glycosylated inasmuch as its apparent size is reduced to 70K daltons after incubation of the brain extract with endoglycosylase F which removes N-linked carbohydrate side chains as discussed by Elder et al., *Proc. Natl. Acad. Sci. USA*, 79 4540–4544 (1982). Thus, the proteinoid translated from the mRNA corresponding to clone plB236 is cellularly derivatized by a glycosylation.

Cell fractionation determinations showed that the immunoreactive 100K dalton proteinoid copurifies with a synaptosomal fraction. Dissection studies showed that this proteinoid is located in the same brain regions as are described in the immunocytochemistry results.

Solublized portions of brain cell tissue extracts were analyzed for the presence of proteinoid derivatives cleaved from the larger proteinoid by the cell. High pressure liquid chromatography (HPLC) and radloimmune assay techniques using antibody receptors raised to the synthetic polypeptides of this invention were used here. Immune-reacting proteinoids in the size range of synthetic polypeptide P5 were detected when anti-P5 serum was used in the assay with the HPLC eluate. This result indicates that the plB236 proteinoid is a precursor for smaller proteinoid derivatives.

Together with the structure of the plB236 proteinoid, the morphological data strongly suggest that this proteinoid is a precursor for a new neuropeptide. The requirements that a polypeptide must meet to be considered a bona-fide neurotransmitter are rather strict, and the evidence that segments of the plB236 proteinoid have a neurotransmitter function is circumstantial and preliminary from the above data. Nevertheless, it is believed that the plB236 proteinoid or one or more of its cellularly processed derivatives are neurotransmitters.

In preliminary studies in which synthetic polypeptides P5 or P8 have been applied iontophoretically in cerebellar Purkinje cells or hippocampal pyramidal cells, the firing rate of those cells where shown to be modified. Tne procedure followed for these studies was analogous to that described by French et al., *Regulatory Peptides*, 1, 127–146 (1980).

More specifically, when P5 at a 1 millimolar concentration was applied by pressure to cortical neurons, there was a decrease in the rate of spontaneous activity as measured by single unit action potentials. Similar application of P5 to cells in the $CA_3$ region of hippocampus resulted in a marked and prolonged increase in the rate of cell firing. Neither effect was noted when other synthetic polypeptides such as P4 were applied similarly. The electrophysical effects of P5 are therefore specific both for the polypeptide and the anatomical localization of the reactive cells.

Preliminary studies with P5 administered intraventricularly into rat brains in an amount of about 5 micrograms per mouse resulted in a significant increase in locomotor activity that was not found with control polypeptides or with saline. The method used for intraventricular administration was analgous to that described by Koob et al., *Regulatory Peptides*, 2, 153–163 (1981).

Synthetic polypeptide P8 which contains the amino acid residue sequence of P6 plus an additional six residues at the amino-terminus of P6 exhibited no electrophysiological effect when administered alone iontophoretically. However, when administered at a 1 millimolar concentration in conjunction with the known excitatory transmitter glutamate (0.5 molar), there was a prolongation of glutamate-induced stimulation. This effect suggests that the natural proteinoid or more likely its derivative corresponding to P8 or P6 provides neuroactivity modulatory action.

The antibodies against the plB236 proteinoids provide useful markers for a major afferent pathway, prominent in cortical regions, regardless of whether the synthetic polypeptides are themselves physiolgically active. As is discussed in more detail hereinafter, neurotransmitter-type activity for the synthetic polypeptides derived from the proteinoid encoded by plB236 has now been shown, and thus this work demonstrates not only a newly discovered major, new neuronal system, but also its putative neurotransmitter.

The amino acid residue sequences of synthetic polypeptides P4, P5, P6, P7, P8, P9 and P10 are represented by the formulas below, from left to right in the direction from amino-terminus to carboxy-terminus, again using the single letter amino acid residue code:

| P4 | LRGQAGAPPRVIC; |
|---|---|
| P5 | NVTESPSFSAGDNPHVLYSPEFRISGAPDKYESE; |
| P6 | LLGLRGEPPELDLSYSHSDLG; |
| P7 | PTKDSYTLTEELAEYAEIRVK; |
| P8 | LGSERRLLGLRGEPPELDLSYSHSDLG; |
| P9 | LLGLRGEPPELDLSYSHSDL-$NH_2$; and |
| P10 | LGSERRLLGLRGEPPELDLSYSHSDL-$NH_2$. |

C. Clone plB208

The plB208 cDNA clone hybridizes to two abundant brain-specific mRNAs that are about 3200 and about 1600 nucleotide bases in length (FIG. 7A). Both mRNAs appear to be coordinately controlled since the relative intensities of the two bands remain approximately constant as the the concentration of each increases in a gradient from forebrain to hindbrain (FIG. 7B). Since the two mRNA species are detected in glioma mRNA but not in PC12 or neuroblastoma mRNA, this is believed to be a clone of glial-specific mRNA. From the intensity of the hybridizations, it is estimated that these two mRNAs species are the two most abundant rat brain-specific mRNAs thus far detected. The difference in the relative hybridization strengths could either reflect that this clone has greater homology to the larger species, or that the two target species are present in different concentrations.

Figure 7D:
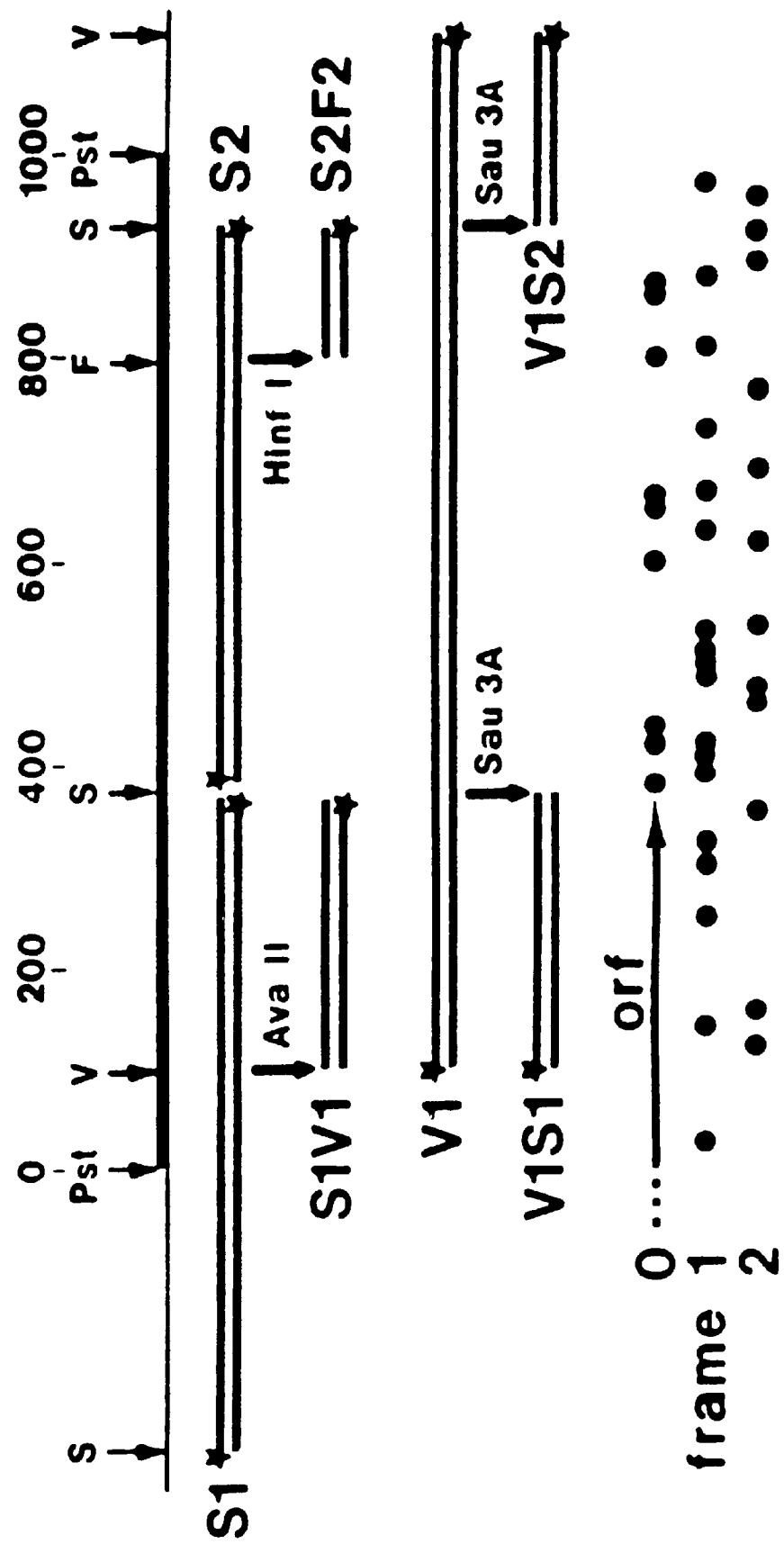
FIG. 7D illustrates the determination of the sense strand and open reading frame of clone 1B208. Details are as described in FIG. 1D. Restriction endonuclease abbreviations are designated as follows: Sau 3A (S) and Ava II (V).

Both mRNAs have a common sense strand (the 978 nucleotide base CDNA insert sequence is shown in FIG. 7C)

as indicated by a determination analogous to that for plA75, and detailed in FIG. 7D and FIG. 7E. Probes complimentary to the 5' end of the sequence (S1V1) hybridized to both target mRNAs. Probes complementary to the 3' end (S2F2) hybridized only to the longer species, thereby indicating that the region of homology between the two mRNAs is in the 5' portion of the sequence. This also indicates that this clone is a copy of a larger mRNA species.

The only sizable orf is unbounded at the 5' end, and runs into the sequence for 121 triplets (FIG. 7D). A putative polypeptide sequence is shown above the nucleotide sequence in FIG. 7C. This putative sequence is not homologous to any proteinoid sequence in the Dayhoff atlas database, above.

As can be seen from the putative sequence, the translated polypeptide is very hydrophobic. Antibodies to this proteinoid have not been pursued.

This hydrophobic polypeptide corresponds to the largest orf in a partial cDNA (978 nucleotides clone of a considerably larger (3200 nucleotides) very abundant glial mRNA. It is believed, from the probable abundance and the hydrophibicity of the putative amino acid residue sequence that the proteinoid encoded from plB208 found in brain cell tissues is glial fibrillary acidic protein (GAFP), a known, prevalent very insoluable 55K dalton glial structural protein about which little is known at the molecular level.

D. Clone p0-40

Figure 8A:
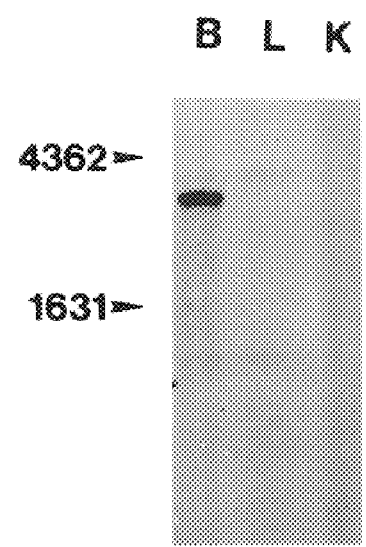
FIG. 8A is a photograph of an autoradiograph illustrating Northern blot analysis of the tissue distribution of p0-40 mRNA. Details are as described in FIG. 1A.

The p0-40 CDNA clone hybridizes to a brain-specific 4000 nucleotide mRNA representing about 0.05 percent of brain mRNA (FIG. 8A). This mRNA has a regional distribution pattern in the brain similar to plA575, except for its relatively lower concentration in cortex where degradation of the mRNA could possibly have occured (FIG. 1B).

The sequence of the p0-40 clone has been determined as it corresponds to a part of a large, brain-specific mRNA (FIG. 8B). The strand corresponding to the mRNA coding strand was identified by determinations analogous to those used for the plA75 clone. Neither the coding nor the non-coding strand of this clone exhibits a long open reading frame (FIG. 8C).

It is possible to derive short open reading frames of similar length to those determined for plA75. However, about 3000 nucleotides are lacking from the mRNA sequence and it is not known how this clone is aligned to bona fide mRNA. As brain-specific mRNAs may have larger than normal non-coding regions, it is believed that this clone may have missed the proteinoid coding region of the corresponding mRNA. This clone was consequently an unlikely choice for further investigation of hypothetical proteinoid products.

E. General Conclusions

Four cDNA clones corresponding to rat brain-specific mRNAs have been studied in detail. The relative regional concentrations of the mRNAs and nucleotide sequences and protein coding strands for each clone have also been determined.

For two clones, the proteinoid products of the mRNA have been identified by chemically synthesizing short polypeptides corresponding substantially to regions predicted from the open reading frames on the sense strand of the mRNA, and by raising antisera to the synthetic polypeptides. The antisera have identified, by immunocytochemistry, the particular subsets of cells within the rat brain which dontain the protein product of the two brain-specific mRNAs, thus indicating that this approach provides a powerful means for describing and locating brain proteinoids and their derivatives. The antipeptide receptors are useful for further studies aimed at localizing those proteinoids or derivatives within the specific cells and for purifying the proteinoid molecules by conventional biochemical and immunoaffinity approaches.

The above-described approach has some features that are in common with strategies for using a monoclonal antibodies to identify specific brain antigens as described by Barnstable, Nature, 286, 231–235 (1982). However, the present approach offers several advantages.

The antisera generated react with predetermined sites (epitopes) within proteinoids or with proteinoid derivatives whose amino acid residue sequences were determined previously, in part by decoding the clonal DNA. In addition, a nucleic acid probe is provided that is already in hand at the time the proteinoid is sought. Thus, if questions about the gene locus, developmental regulation or other details of gene expression arise, the present system is ready for immediate extension.

Furthermore, by demonstrating coincident reactivities of antisera to two synthetic polypeptides from distinct regions of a naturally occurring proteinoid sequence, it is possible to increase the confidence that immunocytochemical reactions occurring at two loci in the brain are a result of the presence of the same proteinoid at those sites. Such is not the case with monoclonal antibodies against brain antigens. Finally, the present approach uses sequence determination as a starting point and as more structural information emerges or becomes interpreted, it is likely that great advances will be made in using sequence to predict function.

Brain-specific mRNAs represent a large portion of brain mRNA content, possibly corresponding to about 30,000 mRNA species, some of which are expressed at a level of about 0.001 percent. For such mRNAs reasonably to play significant biological roles, each must probably be concentrated in a few cell types rather than spread throughout the brain. The proteinoid translation product of the plB236 mRNA is present in a small fraction of brain cells, although its mRNA is estimated to be about 0.01 percent of the total brain mRNA. The immunocytochemical technique appears to have sufficient sensitivity to detect the products of mRNAs expressed at 0.001 percent, given the ease of detection of a proteinoid whose mRNA is tenfold more abundant. Thus, given that Class IV clones correspond the very rare mRNAs in total brain mRNA that are thought to be localized in small subregions of the brain, the proteinoid products of that most interesting class of brain mRNAs may be detectable using the methods described herein.

The proteinoid products of both plA75 and plB236 are present in subsets of brain cells. That different specific genes are turned on in different cell subjects of the brain indicates at the molecular level what was already known at the anatomical level; i.e., the brain is a organ made up of many cell types and neurons are a heterogenous cell class whose members have differentiated from common precursors.

The generally low abundance of brain-specific mRNAs (Class III) relative to mRNAs that are not specifically expressed in brain (Classes I and II), and the potentially large number of very low abundance mRNAs (Class IV) suggest that many brain-specific mRNAs are expressed uniquely in subsets of brain cells that have differentiated from their neuronal stem cells. Therefore, brain-specificity per se is a rather primitive classification.

The present studies, based upon antiserum reactivities, provides a more precise, molecularly-based classification system for cell types. Indeed, this work has already identified two novel brain-specific proteinoids and/or proteinoid derivatives. One proteinoid or its derivative forms an immune reaction with anti-P1 and anti-P2 sera, and is located in the cytoplasm of a large portion of brain cells. It may be involved in the protein synthetic or dendritic transport events exclusive of certain large neurons. The second proteinoid or derivative forms an immune reaction with antisera to P5, P6 and P7, and is present in a discrete pathway of fibers leading from the hindbrain to several distinct anatomical sites. That proteinoid itself, or its brain cell-processed derivatives, has neuroactivity and may be a neurotransmitter.

IV. MATERIALS AND METHODS

A. Complimentary Deoxyribonucleic Acid (cDNA) Cloning and Messenger Ribonucleic Acid (mRNA) Procedures Details of mRNA preparation, cDNA cloning and the selection of brain specific clones are stated below in Sections E and F. For the regional analysis of brain mRNA, rat brains were dissected on ice and extracted as described for total brain mRNA, below. mRNA preparations were separated by electrophoresis on 1.5 percent agarose gels in 1 molar formaldehyde, and transferred to nitrocellulose as described in Thomas, P.S., *Proc. Natl. Acad. Sci. USA*, 77, 5201–5205 (1980). The mRNA preparations were hybridized ("Northern blot") as described in Section G with $^{32}$P-labeled plasmid probes prepared by nick translation as described in Rigby et al., *J. Mol. Biol.*, 113, 237–251 (1977). In some determinations, hybridization probes were end-labeled with $^{32}$P using polynucleotide kinase as described below in Section B.

The procedure described in Cleveland et al., *Cell*, 20, 95–105 (1980) was used for the positive hybridization-translation assay (HART) : mRNA was translated in vitro in a rabbit retuclocyte lysate system (New England Nuclear, Boston, Mass.). Products were analyzed by sodium dodecyl sulfate (SDS) gel electrophoresis as described in Laemmli, U.K., *Nature*, 227, 680–682 (1971).

The rat C6 glioma and mouse C1300 neuroblastoma cell lines were obtained from the American type culture collection; rat pheochromocytoma (PC12) cells were obtained from Dr. Joel Levine of the Salk Institute.

B. Nucleic Acid Sequencing

Using the procedure described in Tanaka et al., *J. Bacteriol.*, 121, 354–362 (1975), plasmid DNA was prepared from chloramphenicol-treated cultures of bacteria carrying the cDNA clones which were identified by the procedure described below in Section F. Aliquots (1 microgram) of each plasmid were digested with each of nine restriction endonucleases having tetra- or penta-nucleotide recognition sequences (Alu I, Bst IV, Hae III, Sau 3a, Hpa II, Hinf I, Ava II, Rsa I, FnuD II). The electrophoresis patterns of the digestion products were compared with those of the plasmid pBR322 as described in Sutcliffe, J. G., *Nucleic Acid Res.*, 5, 2721–2728 (1978) , thereby allowing the identification and sizing of restriction fragments containing the cDNA insert.

Preparative restriction digests (50 microgram) were made with two enzymes that gave 3 or 4 insert-containing fragments. Those fragments were treated with phosphatase, purified on polyacrylamide gels, and were end-labeled with $^{32}$P using polynucleotide kinase. Small aliquots (1 percent) of the end-labeled fragments were digested with several of the enzymes initially screened, and products were displayed on polyacrylamide gels.

From the sizes of the product fragments detected by autoradiography it was generally possible to construct a reasonably accurate restriction map of the insert. This map was used to determine how to cleave the remaining radioactive fragments prior to sequence analysis as described in Maxam et al., *Proc. Natl. Acad. Sci. USA*, 74, 560–564 (1977) such that the resulting data were likely to saturate the insert and, if possible, provide overlaps and duplicate sequence determinations for all regions. Usually, this strategy was sufficient to provide enough sequence data such that only a few specific fragments needed to be prepared for completing a verified insert sequence. This technique allowed several cDNA inserts of 1000–1500 base pairs (bp) to be sequenced in one month. Some of the single end-labeled products of this procedure were used in Northern blots to determine the strandedness of the corresponding mRNAs.

C. Antipeptide Sera

Regions of the cDNA clone plA75 open reading frame (orf) 1 and orf 2, and the cDNA clone plB236 orf were scanned for charged regions in the vicinity of proline residues as described in Sutcliffe et al., *Science*, 219, 660–666 (1983). Corresponding synthetic polypeptides P1, P2, P3 and P4 were prepared as described in Bittle et al., *Nature*, 298, 30–33 (1982). Synthetic polypeptides P5, P6, P7 and P8 were prepared as were polypeptides P1–P4, and were selected because of their potential roles as neuroactive materials (FIG. 5). All polypeptides were used without further purification as their initial use was in obtaining specific antisera.

Each polypeptide was coupled to three carriers, keyhold limpet hemocyanin (KLH), edestin and thyroglobuling by glutaraldehyde treatment: 5 milligrams polypeptide and 5 milligrams carrier protein were suspended in 0.7 milliliters of 0.25 molar sodium phosphate buffer (pH 7.2), incubated with 4 microliters 25 percent glutaraldehyde for 30 minutes at room temperature, and the resulting polypeptide-carrier conjugate was purified by chromatography on Sephadex G-50 (a beaded, cross-linked carbohydrate polymer, Pharmacia Fine Chemicals, Piscataway, N.J.).

The resulting conjugates were used to immunize rabbits. Sera were assayed for antipeptide activity by enzyme-linked immunosorbant assay (ELISA) as described in Green et al., *Cell*, 28, 477–487 (1982).

D. Immunocytochemistry

The procedures for tissue preparation and immunocytochemistry were essentially as described for the detection of beta-endorphin and gamma-melanocyte-stimulating hormone in Bloom et al., *Proc. Natl. Acad. Sci. USA*, 75, 1591–1595 (1978). Rats were anesthetized and perfused transcardially with chilled, freshly depolymerized 5 percent formaldehyde in phosphate buffer (0.3 molar, pH 7.4). After dissection into coronal and sagihal slabs, the tissue was immersed in fixative for 3 hours and passed through increasing concentrations of sucrose (12 to 18 percent) in phosphate buffered saline (Pi/NACl;0.15 molar phosphate buffer, pH 7.4, 0.15 molar NaCl).

Sixty-micron thick sections were cut in a cryostat and collected in Pi/NaCl. These sections were incubated free floating with appropriate dilutions of the primary antibody in Pi/NaCl containing 1 milligram per milliliter bovine serum albumin and 0.3 percent Triton X-100 (polyoxyethylene-9 octyl phenyl ether) , Rohm & Haas Co. (Philadelphia, Pa.) for 12 to 18 hours at 4 degrees C. with continuous vibration. After washing in Pi/NaCl, the sections were incubated for 2 hours at room temperature with vibration along with 2 micrograms per milliliter goat anti-rabbit IgG conjugated to horseradish peroxidase.

After a further washing in Pi/NaCl, the sections were developed with 0.5 percent diaminobenzidine, 0.003 percent $H_2O_2$ for 8 to 15 minutes at room temperature, washed, air dried. They were then examined under a microscope. Some sections were counterstained with cresyl violet or with Richardson's stain to visualize cell nuclei. For preabsorption of the antibodies with polypeptides, dilutions of antibodies were incubated with 60 micrograms per milliliter polypeptide overnight at 4 degrees C. and then applied to tissue sections as described above.

Rats were treated with colchicine to enhance the detection of immunoreactivity in neuronal cell bodies (50 colchicine micrograms per rat in 50 microliters of Krebs-bicarbonate solution 127 millimolar NaCl, 3.83 millimolar KCl, 1.8 millimolar $CaCl_2$, 1.18 millimolar $KH_2PO_4$, 1.18 millimolar Mg $SO_4$, 20 millimolar $NaHCO_3$, 2 grams per liter of d-glucose, 0.1 percent bovine serum albumin, gassed with a mixture of oxygen and carbon dioxide at an $O_2:CO_2$ ratio of 95:5, pH value of 7.4)) by stereotaxic intracisternal injection under chloral hydrate anesthesia. The treated rats were perfused and prepared for immunocytochemistry 48 to 72 hours later by an otherwise unchanged procedure from that above.

When keyhole limpet hemocyanin (KLH) was used as a carrier for polypeptide immunizations, the resulting antisera showed a specific immunoreactivity against cell bodies and fibers in layer V of parietal cortex and other scattered locations that was less intense than the specific anti-synthetic polypeptide reactivities discussed hereinbefore. This reactivity was not blocked by the polypeptide, but could be blocked by preincubation with KLH. Other non-brain related anti-synthetic polypeptide sera in whose preparation KLH was used as carrier show the same immunoreactivity in brain. Therefore, some cells in brain share an antigenic determinant with KLH.

Antisera to polypeptides coupled to the other two carriers used in this study, edestin and thyroglobulin, also exhibited background reactivities. These reactivities were of a very low level when the antisera were used at dilutions of 1:1000 or greater, and gave light reactions with horseradish peroxidase that were easily distinguishable from the intense, punctate horseradish peroxidase deposits of the anti-synthetic polypeptide-specific reactions.

E. Messenger Ribonucleic Acid (mRNA) Preparation

Cytoplasmic messenger ribonucleic acid (mRNA) was isolated from fresh brains, livers, or kidneys of adult male Sprague-Dawley rats (Charles River) by a phenol/chloroform/isoamyl alcohol (50:50:1) extraction as described in Schibler et al., *J. Mol. Biol.*, 142, 93–116 (1980). The extract was then enriched for polyadenylated mRNA [poly $(A)^+$ mRNA] by passage over oligo deoxythymidylate (oligo dT) cellulose as described in Aviv et al., *Proc. Natl. Acad. Sci. USA*, 69, 1408–1412 (1972).

F. Complementary Deoxyribonucleic Acid (cDNA) Cloning cDNA Clones were prepared from brain cytoplasmic poly $(A)^+$ mRNA by modification of the methods of Wickens et al., *J. Biol. Chem.*, 253, 2483–2495 (1978) and Gough et al., *Biochemistry*, 19, 2702–2710 (1980). Reverse transcription was carried out for 60 minutes at 42 degrees C. in a volume of 200 microliters under the following conditions: 50 millimolar Tris (2-Amino-2-hydroxymethyl-1,3-propanediol)-HCl (pH 8.3), 10 millimolar $MgCl_2$, 30 millimolar 2-mercaptoethanol, 70 millimolar KCl, 1 millimolar each of deoxyadenosine triphosphate (dATP), deoxycytidine triphosphate (dCTP), deoxyguanosine triphosphate (dGTP), thymidine triphosphate (TTP), 250 microcuries per milliliter $^{32}$P-dCTP (800 curies per millimule; New England Nuclear, Boston, Mass.), 25 micrograms per milliliter oligo dT, 100 micrograms per milliliter poly $(A)^+$ mRNA, and 1000 units per milliliter of reverse transcriptase. Two variations of this technique were used: (1) for preparation 1, the mRNA was pretreated with 2.5 millimolar $CH_3HgOH$ for 5 minutes at room temperature and actinomycin D (30 micrograms per milliliter) was added to the reaction: (2) for preparation 2, the mRNA was not pretreated and sodium pyrophosphate (4 millimolar) was added to the reaction medium.

After reverse transcription, preparation 1 was first extracted with phenol/chloroform, and then ether. Both cDNA preparations were precipitated several times from the aqueous phases of their reaction media with 0.3 molar sodium acetate and ethanol, dried and resuspended in water. The samples were heated at 100 degrees C. for 3 minutes and chilled rapidly on ice to dissociate mRNA-cDNA hybrids.

Second strand synthesis was carried out for 3 hours at 15 degrees C. in a reaction volume of 200 microliters containing 50 millimolar HEPES [4-(2-hydroxethyl)-1-piperazineethanesulfonic acid], pH 7.2, 70 millimolar KCl, 10 millimolar $MgCl_2$, 10 millimolar dithiothreitol, 0.5 millimolar each dATP, dCTP, dGTP, TTP, and 200 units DNA polymerase I, Klenow fragment [Jacobsen et al., *Eur. J. Biochem.*, 45, 623–627 (1974)] (Bethesda Research Laboratories, Inc., Rockville, Md.). The reaction was stopped by the addition of ethylenediaminetetraacetic acid (EDTA) to a 10 millimolar concentration. The double stranded cDNA (dscDNA) was precipitated with ethanol.

$S_1$ Nuclease digestion was carried out for 30 minutes at 37 degrees C. in a volume of 200 microliters containing 50 millimolar sodium acetate (pH 4.5), 0.3 molar NaCl, 1 millimolar $ZnSO_4$, and 100 units $S_1$ nuclease (PL Biochemicals, Milwaukee, Wis.). After $S_1$ nuclease digestion, the dscDNA preparations were extracted with phenol/chloroform, then ether, and thereafter precipitated from the aqueous phases with 0.3 molar sodium acetate and ethanol.

At this stage, the dscDNA preparations were enriched for larger material on a Biogel A-150 m agrose exclusion chromatography beads (Biorad Laboratories, Richmond, Calif.) in a solution containing 0.15 molar NaCl and 2 millimolar EDTA at pH 8.0, as described in Gough et al., above: preparation 1 was divided into fraction 1A (approximately 1000 to about 1800 base pairs (bp) and 1B (about 500 to about 1000 bp); one fraction, 2A, (greater than about 500 bp) was derived from preparation 2. Oligo deoxycytidine tails (8 to 15 nucleotides) were added to each dscDNA preparation with terminal deoxynucleotide transferase (PL Biochemicals) 1,000 units per milliliter, in 25 micromolar dGTP, 100 millimolar potassium cacodylate (pH 6.9), 2 millimolar $CoCl_2$, 1 millimolar EDTA for 5 minutes at 37 degrees C. as described in Roychoudary et al., *Nucleic Acids Res.*, 3, 865–877 (1976). The tailed dscDNA preparations were extracted with phenol/chloroform, then ether, and precipitated from the aqueous phases with ethanol.

Aliquots of each of the above preparations (10 micrograms per milliliter) were annealed with oligo deoxyguanosine-tailed, endocunluease Pst I-cleaved plasmid pBR322 (10 micrograms per milliliter), in 100 millimolar NaCl, 10 millimolar Tris-HCl, pH 8, 0.5 millimolar EDTA. The mixtures were heated at 67 degrees C. for 10 minutes, 50 degrees C. for 30 minutes and allowed to cool to room temperature overnight. The deoxyguanosine tails of 8 to 15 nucleotides each were added to the cleaved plasmid as described above for deoxycitidine tails.

*E. coli* C600 cells were transformed with the recombinant plasmid, and transformants were selected on tetracycline (10 micrograms per milliliter) plates. Individual colonies were transferred to duplicate ampicillin (33 micrograms per milliliter) and tetracycline plates. Ampicillin sensitive, tetracycline resistant ($Amp^S Tet^r$) colonies were selected for further study.

The colonies were numbered and identified as to the origin of the dscDNA insert used in each case, i.e. from dscDNA insert preparations 1A, 1B, 2A. Clones identified as "pO" originate from a pilot cloning study using the method of Wickens et al., supra.

Amp$^s$ Tet$^r$ clones were grown as 1 milliliter overnight cultures in 2YT (1.6 percent Bacto tryptone, 1 percent Bacto yeast extract and 0.5 percent NaCl in water; Difco Laboratories, Detroit, Mich.) medium and plasmid DNA was extracted by the method dexcribed in Birnboim et al., *Nucleic acids Res.*, 7, 1513 (1979). One-quarter of each culture was digested with Pst I (N.E. Biolabs, Beverly, Mass.) and fractionated on a 1 percent agarose gel using 50 millimolar Tris-borate, pH 8.3, 1 millimolar EDTA in parallel with DNA size standards. Clones giving excisable insert bands of 500 bp or larger were selected for further study.

G. Northern Blot Analysis

Poly (A)$^+$ mRNA samples (usually 2 micrograms) were fractionated by electrophersis on 1.5 percent agarose gels in the presence of 1 molar formaldehyde as described in Rave et al., *Nucleic Acids Res.*, 6, 3559–3567 (1979), and transferred to nitrocellulose as described in Thomas P. S., *Proc. Natl. Acad. Sci. USA*, 77, 5201–5205 (1980). The blots were prehybridized overnight at 42 degrees C. in 50 percent formamide, 0.75 molar NaCl, 25 millimolar PIPES [1, 4-piperazine-bis-(2-ethanesulfonic acid)], pH 6.8, 0.2 percent sodium dodecyl sulfate (SDS), 25 millimolar EDTA, 100 micrograms per milliliter salmon sperm DNA, 100 micrograms per milliliter yeast mRNA and 5X Denhardt's solution as described in Denhardt, D., *Biochem. Biophys. Res. Comm.*, 23, 641–646 (1966). The blots were then hybridized overnight with $^{32}$P-labeled probes at 42 degrees C. in the same medium but with 1X Denhardt's solution.

One-quarter or one-eighth of each crude plasma extract or (for followup screening) 100 nanograms of purified supercoiled plasmid were labeled with $^{32}$P by nick translation as described in Rigby et al., *J. Mol. Biol.*, 113, 237–251 (1977) to specific activities of 2–4×10$^8$ counts per minute per microgram. Blots were washed in two changes of 2X SSC standard sodium citrate solution; 30 millimolar trisodium citrate and 0.3 molar sodium chloride at pH 7.0) 0.2 percent SDS for 60 minutes each at 42 degrees C. and once in 0.1x percent SSC (1.5 millimolar trisodium citrate and 15 millimolar sodium chloride at pH 7.0), 0.2 percent SDS for 15 minutes at 67 degrees C. The washed blots were then exposed to Kodak XRP-5 or XAR-1 X-ray film at minus 50 degrees C. using Cronex Lightening Plus intensification screens for 1 or 14 days. Size estimates were based on comparisons with plasmid pBR322 standards as described in Sutcliffe, J. G., *Nucleic Acids Res.*, 5, 2721–2728 (1978).

H. Southern Blot Analysis

DNA was extracted from rat liver nuclei after treatment with proteinase K and SDS, digested with Hind III or Eco RI restriction endonucleases, and fractionated on 0.6 percent agarose gels. The DNA was transferred to nitrocellulose as described in Southern, E., *J. Mol. Biol.*, 98, 503–517 (1975) and hybridized with $^{32}$P labeled probes as described for Northern blots.

I. Western Blot Analysis

The general method described in Towbin et al., *Proc. Natl. Acad. Sci. USA*, 76, 4350–4354 (1979) was followed. Rat brain homogenates were pelleted by centrifugation at 20,000 times the force of gravity (Xg) for 20 minutes to provide a crude mitochondrical-synaptosomal pellet. Less than about 10 percent of the total immunoreactivity remained in the supernatant after centrifugation.

The pelleted material was then separated electrophoretically on an 8 percent polyacrylamide-SDS gel, followed by electroblotting onto nitrocellulose. The blotted fractions were then admixed with appropriate anti-synthetic polypeptide antibodies, e.g. anti-P5, -P6 or -P7 sera. Visualization of bound antibody was accomplished using goat anti-rabbit IgG conjugated to HRP as the indicating group, using diaminobenzidine and hydrogen peroxide as discussed hereinbefore.

J. mRNA Abundance Measurements

Recombinant plasmid DNA from 11 clones was prepared from chloramphenicol-treated bacterial cultures by the method described in Tanaka et al., supra, and 10 micrograms of purified DNA from each clone were denatured and immobilized on duplicate nitrocellulose filters as described in Melli et al., *J. Mol.:Biol.*, 93, 23–38 (1975). Brain cytoplasmic poly (A)$^+$ mRNA (4 micrograms) was broken with alkali by incubation at 90 degrees C. for 15 minutes in 50 microlites 10 millimolar Tris, pH 9.5, 1 millimolar spermidine, 0.1 millimolar EDTA and end-labeled by incubation at 37 degrees C. for 60 minutes with 6 microliters 0.5 molar Tris (pH 9.5) 0.1 MgCl$_2$, 50 millimolar dithiothreitol, 50 percent glycerol, containing 0.5 microcuries –$^{32}$ P-ATP (2000 curies per millimole) and T4 polynucleotide kinase (4 units) to give a product mRNA population of approximately 100 nucleotides.

The $^{32}$P-mRNA was hybridized to the plasmid DNA, the nitrocellulose filters were washed and treated with pancreatic mRNAase and proteinase K under the same conditions as described in Derman et al., *Cell*, 23, 731–379 (1981). The filters were counted, and the percent of steady state poly (A)$^+$ mRNA hybridizing to each clone was calculated using the following formula:

$$\frac{\text{number average of mRNA size} \times (\text{hybrid-background}) \text{cpm} \times 1.5 \times 100}{\text{cDNA insert size total cpm}}$$

The number average size (1760 nucleotides) was used to obtain a number percent rather than a weight percent. The factor 1.5 was used because the poly(A)$^+$ mRNA preparation was judged to be contaminated by about 30 percent ribosomal mRNA.

The calculated abundance was rounded off into one of the abundance classes; 3.0, 2.0, 1.0, 0.5, 0.2, 0.1, 0.05, 0.02, 0.01 percents. The abundances of the other clones was estimated by comparison with these 11 standards, using probe-specific activity, autoradiograph exposure times and band intensity as bases for estimates.

K. High Pressure Liquid Chromatography

Analyses by high pressure liquid chromatography (HPLC) were carried out using a Waters Associates Model 204 liquid chromatograph containing a PAC I-125 column (Waters.Associates, Boston, Mass.) generally following the techniques outlined in Rivier, *J. Chromatogr.*, 202, 211–222 (1980). Elution was carried out in an aqueous buffer containing 0.25 molar triethylamine phosphate (pH 2.25) and 30 percent acetonitrile.

Samples applied in HPLC contained 100 microliters of a 1 molar acetic acid extract of rat brain (4 brains/milliliter). The fractions obtained were analyzed for the formation of an immune reaction with anti-P5, -P6 and -P7 activity by the use of $^{125}$I-labeled sera.

The assays so performed had a sensitivity of 20–50 picograms of proteinoid derivative. Preliminary studies showed the majority of anti-P5 activity to elute from the column with the retention time of a small polypeptide containing about 15 to about 40 amino acid residues. Synthetic polypeptide P5 had a similar elution time.

The elution pattern obtained showed that several, relatively low molecular weight proteinoid derivatives with anti-P5 reactivity were present, thereby indicating an amino acid residue sequence corresponding substantially to that of synthetic polypeptide P5 was present in those eluted fractions that could form an immune reaction with anti-P5 serum. That result thereby indicates the presence of an amino acid residue sequence corresponding substantially to that of synthetic polypeptide P5 may be present in a plurality of the eluted fractions.

L. Intraventricular Administration

Rats were equipped with an intracerebroventricular cannula aimed above the lateral ventricle for intraventricular administrations of the synthetic polypeptides. The general procedure of Koob et al., *Regulatory Peptides*, 2, 153–163 (1981) was followed.

For this surgery, rats were anesthetized with chloropent anesthesia (Fort Dodge Laboratories, Inc.) and secured in a Kopf stereotaxic instrument. A guide cannula, made of 23 gauge stainless steel tubing and 7 millimeters long was lowered to within 1 millimeter of the ventricle and anchored to the skull with two stainless steel screws and dental cement. Coordinates were, with the tooth bar 5 millimeters above interaural zero, −0.6 millimeters posterior to bregma, 2.0 millimeters lateral and −3.2 millimeters below skull surface at the point of entry.

For an injection, the dummy stylet was removed and a 30 gauge stainless steel cannula with 30 centimeter of polyethylene 10 tubing attached was inserted through the guide to 1 millimeter beyond the guide tip. One microliter of solution containing 5 micrograms of polypeptide was injected by gravity over a 30 second period by raising the tubing above the head of the rat until flow began. Volume was measured by marks on the polyethylene 10 tubing previously calibrated with a 5 microliter Hamilton syringe.

Only those rats whose cannulae flowed easily with this technique were used in the study. All experiments were performed using a blind procedure where the person testing the rats was unaware of the subject's treatment.

V. SPECIFIC EMBODIMENTS OF THE INVENTION

A. Synthetic Polypeptides

One embodiment of this invention is a synthetic polypeptide. That synthetic polypeptide corresponds in amino acid residue sequence to at least a portion of the sequence of a naturally occurring proteinoid, and has a molecular weight equal to less than that of the proteinoid. The proteinoid itself contains an amino acid residue sequence that is translated from a messenger RNA (mRNA) present substantially only in brain cells. The synthetic polypeptide when bound to a carrier as a conjugate and introduced into an animal induces the production of antibodies that bind to the naturally occurring proteinoid or a derivative of that proteinoid in an an immune reaction.

Exemplary of such synthetic polypeptides are synthetic polypeptides P1, P2 and P5–P10, discussed hereinbefore. That previous discussion illustrated that the sequences of the synthetic polypeptides corresponded substantially to portions of the sequences of the proteinoids translated by the cell from mRNAs that hybridized with clone plA75 or clone plB236, and that the molecular weights of the synthetic polypeptides were substantially less than the proteinoid molecular weights. This is easily seen from the 318 amino acid residue sequence of the clone plB236 reading frame of the proteinoid and the 34-mer and 21-mer polypeptides of synthetic polypeptides P5 and P6, respectively.

The presence of mRNA that is cellularly translated into a proteinoid has been illustrated by the in vitro mRNA-stimulated proteinoid synthesis using mRNAs from various tissues. The mRNA that is present substantially only in brain cell tissue and is translated into the naturally occurring proteinoid is preferably polyadenylated, and is present in the cytoplasin as compared to the nucleus or a mitrochondria.

The messenger RNA that is translated into the naturally occurring proteinoid is preferably an mRNA that is present at a concentration of less than about 2 percent by weight of the brain cytoplasmic messenger mRNA. More preferably, the mRNA translated into the proteinoid is present at less than about 0.2 weight percent, and most preferably at less than about 0.01 weight percent, of the cytoplasmic mRNA of the brain.

Several synthetic polypeptides were bound to carriers such as KLH, edestin and thyroglobulin to form conjugates, and. the conjugates so formed were used to induce the production of antibodies in animals. The synthetic polypeptides so used are preferably at least about 6 amino acid residues long and can be of almost any length less than that of the proteinoid. However, it is preferred that the synthetic polypeptide about 10 to about 50 amino acid residues in length. It is also noted that the synthetic polypeptide can be used alone, inter alia, for raising antibodies and therapeutically, although it is preferred to use a conjugate when antibodies are to prepared.

Binding of the antibodies so raised has been illustrated by the cytoimmunochemical determinations and HPLC-fractionated proteinoid derivative determinations discussed before. The proteinoid or proteinoid derivative bound by the antibodies so prepared is preferably a proteinoid that is itself neuroactive or is processed in the cell into one or more neuroactive proteinoid derivatives as is the material bound by antibodies to synthetic polypeptides P5 and P6. In addition, it is preferred that the synthetic polypeptide itself be neuroactive, as is synthetic polypeptide P5, or have a modulating effect on neuroactivity as does synthetic polypeptide P8.

Specific synthetic polypeptides of this invention are exemplified by synthetic polypeptides P1, P2 and P5–P10 whose amino acid residue sequences have been described hereinbefore.

B. Receptor Molecules

Biologically active receptor molecules constitute another embodiment of this invention. These molecules are antibodies, or idiotype-containing polyamide portions of antibodies, induced or raised to a synthetic polypeptide of this invention or to its conjugate with a carrier. In preferred practice, the receptors are raised to the preferred synthetic polypeptides of this invention.

The receptors are biologically active in that they bind at least with the antigenic synthetic polypeptide when admixed therewith in aqueous solution, at least at physiological pH values and ionic strengths. Preferably, the receptors also bind with the naturally occurring proteinoid or a derivative of that proteinoid under the same conditions when the proteinoid or its derivative are within brain cell tissue, on the surface of such tissue or when brain cell tissue is suspended or dissolved in an aqueous medium. It is more preferred that the receptors bind at least to the antigenic synthetic polypeptide within a pH value range of about 5 to about 9, and at ionic strengths such as that of distilled water to that of about one molar sodium chloride.

Idiotype-containing polyamide portions of antibodies are the portions of antibodies that bind to an antigen. Such portions include the Fab, Fab', and F(ab')$_2$ fragments prepared from antibodies by well-known enzymatic cleavage techniques. Inasmuch as antibodies are discussed in the art as being "raised" or "induced", idiotype-containing polyamide portions of antibodies will also be discussed herein as being "raised" or "induced" with the understanding that a subsequent cleavage step is normally required to prepare such materials from antibodies.

The receptor molecules may be polyclonal as is the case for the antibodies discussed hereinbefore, or the receptors may be monoclonal. Techniques for preparing monoclonal antibodies are well known, and monoclonal receptors of this invention may be prepared by using the synthetic polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier.

Receptors are utilized along with an "indicating group" also sometimes referred to as a "label". The indicating group or label is utilized in conjunction with the receptor as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The indicating group may be bonded to the receptor as where an antibody is labeled with $^{125}$I. The indicating group may also constitute all or a portion of a separate molecule or atom that reacts with the receptor molecule such as HRP-linked to goat anti-rabbit antibodies where the antibody receptor was raised in a rabbit, or where a radioactive element such as $^{125}$I is bonded to protein A obtained from *Staphylococcus aureus*.

Where the principal indicating group is an enzyme such as HRP, additional reagents are required to visualize the fact that an immune reaction has occurred. Such additional reagents for HRP include hydrogen peroxide and an oxidation dye precursor such as diaminobenzidine, used herein.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

C. Assay for the Presence of Amino Acid Residue Sequences

Another embodiment of this invention relates to an assay for the presence of a naturally occurring amino acid residue sequence of a brain cell proteinoid. Here, an above-described receptor is raised and harvested. The receptor (antibody or idiotype-containing polyamide portion thereof) is then admixed with brain tissue and an indicating group. The presence of the naturally occurring amino acid residue sequence is ascertained by the formation of an immune reaction as signaled by the indicating group.

This method is applicable to solid phase systems such as the brain cell tissue sections described before using antibodies raised to synthetic polypeptides P1 and P2. This method is particularly useful for assaying for the presence of neuroactive proteinoids, or their derivatives whose mRNAs are present in relatively small amounts, as was shown with antibodies induced by the introduction of synthetic polypeptides P5 and P6 into rabbits. It is also useful in liquid media such as homogenized or other brain cell tissue preparations, as was shown for the HPLC-fractionated proteinoid derivatives.

One particular liquid medium in which a receptor of this invention is useful is cerebrospinal fluid (CSF). The CSF may be utilized alone as an aqueous liquid medium or admixed with water or a buffer solution diluent.

In a further embodiment of the invention, cerebrospinal fluid from an animal with a suspected brain injury is provided. When a brain injury occurs, such CSF typically contains a proteinoid or proteinoid derivative released from the injured brain cell tissue due to the connection between the brain and spinal cord.

An aliquot of the CSF so provided is admixed with an effective amount of a biologically active receptor and an indicating group, or a panel of a plurality of different receptors and appropriate indicating groups. The admixture is typically incubated as is known, for a time sufficient to permit an immune reaction to occur. The incubated admixture is then assayed for the presence of an immune reaction as indicated by the indicating group. The presence of the proteinoid or its derivative is thereby shown and provides evidence of an injury to brain tissue.

Where the proteinoid or proteinoid derivative being assayed is a normal constituent of CSF, this technique is used to measure an increase in the amount present. In this embodiment, an increase in the amount of proteinoid or its derivative indicates an injury to brain tissue or an abnormality in the brain tissue leading to that increase.

Receptors raised to a synthetic polypeptide having an amino acid residue sequence corresponding substantially to the sequence of a proteinoid or proteinoid derivative translated from an mRNA present substantially only in specific types of brain cell tissues or in cells of tissue located at a known site in the brain are used in one aspect of this embodiment. Utilization of such receptors thereby permits the user to identify the type of tissue injured or to locate the site or sites of injury to the brain without resort to surgery.

For example, receptors such as the antibodies induced by introduction of synthetic polypeptide P1 into a rabbit, described above, may be utilized to detect an injury to neurons and dendritic processes throughout the brain. A known amount of those receptors is admixed with a CSF aliquot that is thought to contain the proteinoid encoded by the DNA of clone p1A75, and the admixture is preferably incubated to permit an immune reaction to take place. Wells of a microtiter plate are coated with a known amount of synthetic polypeptide P1. The admixture is then added to the wells, incubated, and rinsed. A known amount of goat anti-rabbit HRP-linked antibodies is then added to the microtiter plates along with requisite amounts of hydrogen peroxide and diaminobenzidene. The extent of the ensuing reaction is then used along with appropriate standards as an assay for the presence and amount of the proteinoid in the CSF, and thereby as an assay to determine whether the anti-P1 reactive neurons and dendritic processes were injured. It can be readily seen that a similar technique can be used for proteinoids or their derivatives that are anatomically regionalized as an assay for a brain site-specific injury assay.

It is to be understood that the specificity of this method may be broad, so as to permit an assay for injury to the brain generally, or the specificity may be narrowed to enable one to locate the site of the injury more closely. When broad specificity is desired, receptors raised to a synthetic polypeptide whose amino acid residue sequence corresponds to the sequence of a widely distributed proteinoid or proteinoid derivative such as is the case for receptors raised to synthetic polypeptides P1 or P2 are used. Narrowed specificity as to tissue-type injury may be obtained using receptors such as those raised to synthetic polypeptides P5, P6 or P7.

A diagnostic system, preferably in kit form, comprises yet another embodiment of this invention. This system is useful for assaying the presence of a naturally occurring amino acid residue sequence of a proteinoid or its derivative in brain cells by the formation of an immune reaction. This system includes at least one package that contains a biologically active receptor of this invention.

An indicating group or label is preferably supplied along with the receptor and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Each diagnostic system may be designed for assaying the presence of different amino acid residue sequences. Thus, a system utilized for assaying for the presence of a neuroactive proteinoid or a neuroactive derivative thereof may contain anti-synthetic polypeptide P5, anti-synthetic polypeptide P6 or anti-synthetic polypeptide P7 receptors. Similarly, a system for assaying for the presence of large projection neurons such as pyramidal cells may contain anti-synthetic polypeptide P1 or anti-synthetic polypeptide P2 receptors.

D. Pharmaceutical Compositions

Several synthetic polypeptides of this invention are neuroactive; i.e., the polypeptides alter the activity of brain cells amid their surroundings when administered to these cells. Synthetic polypeptides P5 and P8 were shown hereinbefore to possess a neurotransmitter-like activity (P5) and neuromodulating activity (P8), respectively. Thus, synthetic polypeptide P5 was shown to increase the firing rate of cells of the $CA_3$ region of the hippocampus when administered iontophoretically and was found to increase the daytime motor activity of rats when given intraventricularly. Consequently, both synthetic polypeptides P5 and P8 have biological, neuroactivity in the brain that can be measured neurphysiologically and/or behaviorally. In addition, synthetic polypeptide P8 was shown to modulate neuroactivity in the presence of glutamate.

A pharmaceutical composition of this invention includes a synthetic polypeptide of this invention along with a physiologically acceptable diluent such as distilled or deionized water, normal saline, Krebs-bicarbonate solution or the like.

The synthetic polypeptides of this invention may be administered directly into the brain, e.g., intraventricularly, or they may be administered into the CSF as by injection. Typical effective dosages range from about 0.10 micrograms/kilogram of body weight to about 100 micrograms/kilogram of body weight.

Pharmaceutical compositions that contain the synthetic polypeptides as a "pro-polypeptide" may also be administered intravenously (i.v.) or subcutaneously (s.c.). The term "pro-polypeptide" as used herein refers to a derivatized form of a synthetic polypeptide of this invention, which after administration to an animal is altered within the animal's body to release the synthetic polypeptide or a biologically active derivative of the synthetic polypeptide at the therapeutic site or sites, especially the brain.

The pro-polypeptide is preferably a lipophilic derivative of the synthetic polypeptide. The synthetic lipophilic polypeptide derivative is capable of passage from the blood stream through the blood-brain barrier and into brain cell tissues to facilitate i.v. and/or s.c. administration.

Pro-polypeptides may be prepared using known reagents that diminish or eliminate the ionic charge that is otherwise normally present on the synthetic polypeptide. For example, the synthetic polypeptide N-terminal amino groups and lysine epsilon-amino groups may be reacted with reduced N-methyl nicotinic acid or the like to change the positive ionic charge normally present on those amines at physiological pH values to amide groups that are neutral in charge. The nicotinic acid moiety may also be reduced after the amide-forming reaction is completed.

The reduced form of N-substituted nicotinic acid moiety is more lipophilic than the above amino groups, and has been shown by Bodor, *Science,* 214, 1370–1372 (1981) to be useful in derivatizing a primary amino group-containing drug model to permit passage of the derivatized model through the blood-brain barrier. Oxidation to a charged species occurs within brain cells, and the resulting charged drug model derivative remains within the brain wherein it can be processed into the underivatized drug model. The same reaction sequence is thought to occur with the reduced nicotinamide derivatized synthetic polypeptides of this invention.

Amino groups may also be made more lipophilic by amidification reactions with reactive acids containing 1 to about 10 carbon atoms. Exemplary of such acids are formic acid, acetic acid, pivalic acid, benzoic acid and the like. The acids may be made "reactive" by the use of their acid chlorides, or anhydrides, by the use of a carbodiimide coupling agent such as 1-ethyl-3-(3-dimethylamino)-propyl carbodiimide, or the like, as is well known.

The positive ionic charge on amino groups may also be eliminated by reactions which change those amines into carbamate linkages. Thus, the amino groups may be reacted with ethyl chloroformate to form the ethyl carbamate (N-carbethoxy) derivatives.

The negative ionic charge of a carboxy group may be neutralized by the formation of amide or ester linkage to provide a pro-polypeptide that is relatively more lipophilic than the synthetic polypeptide itself.

As was noted hereinbefore, several neuroactive polypeptides found in the brain and elsewhere in the body contain carboxy-terminal amido groups. Such unsubstituted carboxy-terminal amido groups ($—CONH_2$) are preferred herein for providing the carboxy-terminal portions of the pro-polypeptides of this inventions.

Mono- and disubstituted carboxy-terminal amides are also useful wherein the amido nitrogen atom is substituted with a lower alkyl group containing 1 to about 4 carbon atoms, a hydroxy-substituted lower alkyl or wherein the amido nitgrogen atom forms a five- or six-membered ring that may contain one or more heteroatoms such as oxygen, sulfur or nitrogen.

Stated differently, the carboxyl function of the carboxy-terminal amino acid residue of a pro-polypeptide may be an amide derivative of the formula $—CONR^1R^2$ wherein $R^1$ and $R^2$ are independently hydrogen, $C_1$–$C_4$ alkyl, $C_1$ –$C_4$ hydroxyalkyl, or $R^1$ and $R^2$ taken together along with the amido-nitrogen form a five- or six-membered ring that may contain one or more heteroatoms selected from the group consisting of oxygen, sulfur and nitrogen. Examplary $C_1$–$C_4$ alkyl redicals include methyl, ethyl, iso-propyl, sec-butyl and the like. Exemplary $C_1$–$C_4$ hydroxyalkyl radicals include 2-hydroxyethyl, 2-hydroxypropyl, 3-hydroxypropyl, and the like. Exemplary five- and six-membered ring radicals, including the amido-nitrogen, include pyrazinyl, pyrazolidyl, pyridyl, mopholinyl, thiomorpholinyl, pyrolidinyl, triazolyl, triazinyl, and the like.

Sugar molecules such as glucose or ribose may be used as the alcohol portion of ester derivatives of the carboxy-terminal amino acid residue or of any other carboxy group-containing amino acid residue. Mono-functional alcohols containing 1 to about 10 carbon atoms such as methanol, ethanol, benzyl alcohol and the like are also useful in forming ester-containing pro-polypeptides. In addition, pivaloyloxymethyl esters and the like can be prepared by reaction of potassium carboxylate salts with chloromethyl pivalate or another, similar chloromethyl ester such as chloromethyl acetate.

The above-described reactions and derivatizing agents are intended to be exemplary of those which may be used. The use of any specific reaction or derivatizing agent is not a part of this invention except as that reaction or agent is used to provide pro-polypeptides that are more lipophilic than are the synthetic polypeptides of this invention themselves, such that after s.c. or i.v. administration, the pro-polypeptides so prepared pass from the blood stream through the blood-brain barrier and into the brain with greater facility than do those synthetic polypeptides.

The foregoing is intended as illustrative of the present invention but not limiting. Numerous variations and modifications may be effected without departing from the true spirit and scope of the novel concepts of the invention.

What is claimed is:

1. A receptor that specifically binds to brain cell tissue comprising an isolated and purified antibody or epitope-binding portion thereof raised to a synthetic polypeptide about 10 to about 50 amino acid residues in length or a conjugate of that synthetic polypeptide bound to a carrier, said synthetic polypeptide having
   (a) a determined amino acid residue sequence substantially corresponding to an amino acid residue sequence of at least a portion of a naturally occurring proteinoid, and
   (b) a molecular weight equal to less than that of said proteinoid,
   said proteinoid containing an amino acid residue sequence that is translated from a cytoplasmic messenger RNA present in brain cells but not in the cells of the liver, kidney, gut, lung, heart, or skeletal muscle of the same species of mammal, said receptor binding specifically to said synthetic polypeptide and to said proteinoid when admixed with brain cell tissue including said naturally occurring proteinoid.

2. The receptor of claim 1 wherein said synthetic polypeptide has an amino acid residue sequence as represented by a formula below; from left to right and in the direction from amino-terminus to carboxy-terminus, said sequence being selected from the group consisting of
   (a) CIPEGLESYYTEQ
   (b) RSVSPWMSVLSEE
   (c) NVTESPSFSAGDNPHVLYSPEFRISGAPDKYESE;
   (d) LLGLRGEPPELDLSYSHSDLG;
   (e) PTKDSYTLTEELAEYAEIRVK;
   (f) LGSERRLLGLRGEPPELDLSYSHSDLG;
   (g) LLGLRGEPPELDLSYSHSDL—$NH_2$; and
   (h) LGSERRLLGLRGEPPELDLSYSHSDL—$NH_2$.

3. A receptor that specifically binds brain cell tissue comprising an isolated and purified antibody or epitope-binding portion thereof reactive to a predetermined epitope and raised to a synthetic polypeptide about 10 to about 50 amino acid residues in length or a conjugate of that synthetic polypeptide bound to a carrier, said synthetic polypeptide having
   (a) an amino acid residue sequence corresponding substantially to an amino acid sequence of at least a portion of a naturally occurring neuroactive proteinoid, and
   (b) a molecular weight equal to less than that of said proteinoid,
   said proteinoid containing an amino acid residue sequence that is translated from a messenger RNA present in the cytoplasm and not in the nucleus or mitochondria of mammalian brain cells at less than about 0.2 percent by weight of the brain cytoplasmic messenger RNA and is not present in the cells of the liver, kidney, gut, lung, heart or skeletal muscle of the same species of mammal, said receptor binding specifically to said synthetic polypeptide and to said proteinoid when admixed with brain cell tissue including said naturally occurring proteinoid.

4. The receptor according to claim 3 wherein said messenger RNA present substantially only in cells of brain tissue is present at less than about 0.01 weight percent of said brain cycoplasmic messenger RNA.

5. The receptor according to claim 1 wherein said isolated and purified antibody or epitope-binding portion thereof is polyclonal.

6. The receptor according to claim 1 wherein said isolated and purified antibody or epitope-binding portion thereof is monoclonal.

7. The receptor according to claim 3 wherein said isolated and purified antibody or epitope-binding portion thereof is polyclonal.

8. The receptor according to claim 3 wherein said isolated and purified antibody or epitope-binding portion thereof is monoclonal.

9. An isolated antibody or proteinoid-binding fragment thereof that specifically binds a proteinoid comprising the amino acid residue sequence represented by a formula below, from left to right and in the direction from amino-terminus to carboxy-terminus, the formula of said sequence being:
   (a) CIPEGLESYYTEQ, or
   (b) RSVSPWMSVLSEE.

10. A receptor that specifically binds to brain cell tissue comprising an isolated and purified antibody or epitope-binding portion thereof raised to a synthetic polypeptide about 10 to about 50 amino acid residues in length or a conjugate of that synthetic polypeptide bound to a carrier, said synthetic polypeptide having
   (a) a determined amino acid residue sequence substantially corresponding to an amino acid residue sequence of at least a portion of a naturally occurring proteinoid,
   (b) a molecular weight equal to less than that of said proteinoid, and
   (c) said synthetic polypeptide having an amino acid residue sequence as represented by a formula, from left to right and in the direction from amino-terminus to carboxy-terminus, that is selected from the group consisting of (a) CIPEGLESYYTEQ;
(b) RSVSPWMSVLSEE;
(c) NVTESPSSFSAGDNPHVLYSPEFRISGAPDKYESE;
(d) LLGLRGEPPELDLSYSHSDLG;
(e) PTKDSYTLTEELAEYAEIRVK;
(f) LGSERRLLGLRGEPPELDLSYSHSDLG;
(g) LLGLRGEPPELDLSYSHSDL—NH$_2$; and
(h) LGSERRLLGLRGEPPELDLSYSHSDL—NH$_2$, said proteinoid containing an amino acid residue sequence that is translated from a cytoplasmic messenger RNA present in brain cells but not in the cells of the liver, kidney, gut, lung, heart, or skeletal muscle of the same species of mammal, said receptor binding specifically to said proteinoid or a derivative thereof when admixed with brain cell tissue including said naturally occurring proteinoid or a derivative thereof.

* * * * *